US010016514B2

(12) United States Patent
Keimel et al.

(10) Patent No.: US 10,016,514 B2
(45) Date of Patent: Jul. 10, 2018

(54) POLYNUCLEOTIDES, VECTORS AND METHODS FOR INSERTION AND EXPRESSION OF TRANSGENES

(71) Applicant: New Hope Research Foundation, North Oaks, MN (US)

(72) Inventors: John G. Keimel, North Oaks, MN (US); Michael David Kaytor, Maplewood, MN (US)

(73) Assignee: New Hope Research Foundation, North Oaks, MN (US)

( * ) Notice: Subject to any disclaimer, the term of this patent is extended or adjusted under 35 U.S.C. 154(b) by 0 days.

(21) Appl. No.: 15/145,293

(22) Filed: May 3, 2016

(65) Prior Publication Data

US 2016/0331846 A1 Nov. 17, 2016

Related U.S. Application Data

(60) Provisional application No. 62/162,199, filed on May 15, 2015.

(51) Int. Cl.
| | |
|---|---|
| *C12N 15/74* | (2006.01) |
| *A61K 48/00* | (2006.01) |
| *C12N 15/86* | (2006.01) |
| *A61K 38/47* | (2006.01) |
| *C12N 9/24* | (2006.01) |
| *A61K 35/761* | (2015.01) |
| *C12N 15/67* | (2006.01) |
| *C12N 15/85* | (2006.01) |
| *C12N 15/864* | (2006.01) |
| *A61K 38/00* | (2006.01) |

(52) U.S. Cl.
CPC ........ *A61K 48/0066* (2013.01); *A61K 35/761* (2013.01); *A61K 38/47* (2013.01); *C12N 9/2402* (2013.01); *C12N 15/67* (2013.01); *C12N 15/85* (2013.01); *C12N 15/86* (2013.01); *C12N 15/8645* (2013.01); *C12Y 302/01052* (2013.01); *A61K 38/00* (2013.01); *C12N 2750/14143* (2013.01); *C12N 2830/34* (2013.01); *C12N 2830/42* (2013.01)

(58) Field of Classification Search
None
See application file for complete search history.

(56) References Cited

U.S. PATENT DOCUMENTS

| | | | |
|---|---|---|---|
| 4,373,071 A | 2/1983 | Itakura | |
| 4,401,796 A | 8/1983 | Itakura | |
| 4,458,066 A | 7/1984 | Caruthers et al. | |
| 4,598,049 A | 7/1986 | Zelinka et al. | |
| 5,139,941 A | 8/1992 | Muzyczka et al. | |
| 6,040,172 A | 3/2000 | Kaplitt | |
| 6,180,613 B1 | 1/2001 | Kaplitt et al. | |
| 6,468,524 B1 | 10/2002 | Chiorini et al. | |
| 6,503,888 B1 | 1/2003 | Kaplitt et al. | |
| 6,555,674 B2 | 4/2003 | Tornøe et al. | |
| 6,582,692 B1 | 6/2003 | Podsakoff et al. | |
| 6,686,168 B1* | 2/2004 | Lok ........................ | C07H 21/04 435/252.3 |
| 7,465,583 B2 | 12/2008 | Samulski et al. | |
| 7,790,154 B2 | 9/2010 | Samulski et al. | |
| 7,968,698 B2 | 6/2011 | Kadonaga et al. | |
| 8,198,079 B2 | 6/2012 | Clements et al. | |
| 8,419,710 B2 | 4/2013 | Keimel et al. | |
| 9,150,882 B2 | 10/2015 | Kay et al. | |
| 2002/0098547 A1* | 7/2002 | Tornoe .................. | C12N 15/85 435/69.1 |
| 2015/0258180 A1 | 9/2015 | Mahuran et al. | |

FOREIGN PATENT DOCUMENTS

| | | |
|---|---|---|
| CA | 2888628 | 4/2014 |
| WO | 0212514 | 2/2002 |
| WO | 2005039643 | 5/2005 |
| WO | 2010082622 | 7/2010 |
| WO | 2012115980 | 8/2012 |
| WO | 2012177997 | 12/2012 |
| WO | 2013173129 | 11/2013 |
| WO | 2014077863 | 5/2014 |
| WO | 2015150922 | 10/2015 |
| WO | 2016187053 | 11/2016 |

OTHER PUBLICATIONS

"International Search Report and Written Opinion," for PCT/US2016/032496 dated Jul. 28, 2016 (13 pages).
Bevan, Adam K. et al., "Systemic Gene Delivery in Large Species for Targeting Spinal Cord, Brain, and Peripheral Tissues for Pediatric Disorders," Molecular Therapy, vol. 19, No. 11 (Nov. 2011), pp. 1971-1980 (10 pages).
Blazeck, John et al., "Promoter Engineering: Recent Advances in Controlling Transcription at the Most Fundamental Level," Biotechnology Journal (2013), vol. 8, pp. 46-58 (13 pages).
Boulaire, Jerome et al., "Transcriptional Targeting to Brain Cells: Engineering Cell Type-Specific Promoter Containing Cassettes for Enhanced Transgene Expression," Advanced Drug Delivery Reviews (2009), vol. 61, pp. 589-602 (14 pages).

(Continued)

Primary Examiner — James S Ketter
(74) Attorney, Agent, or Firm — Pauly, DeVries Smith & Deffner LLC

(57) ABSTRACT

Embodiments herein include polynucleotides, vectors and methods for the insertion and expression of transgenes. In an embodiment, a polynucleotide is included. The polynucleotide can include a JeT promoter or variant thereof, an intron sequence less than 400 bases in length, and a polynucleotide sequence encoding a polypeptide or protein operatively linked to the promoter. In an embodiment, a recombinant vector is included. The recombinant vector can include a JeT promoter or variant thereof, an intron sequence less than 400 bases in length, and a polynucleotide sequence encoding a polypeptide or protein operatively linked to the promoter. Other embodiments are also included herein.

20 Claims, 7 Drawing Sheets

(56) References Cited

OTHER PUBLICATIONS

Bryson, Christine J. et al., "Prediction of Immunogenicity of Therapeutic Proteins," Biodrugs, vol. 24, No. 1 (2010), pp. 1-8 (8 pages).
Burke, Thomas W. et al., "*Drosophila* TFIID Binds to a Conserved Downstream Basal Promoter Element That is Present in Many TATA-Box-Deficient Promoters," Genes Dev (1996), vol. 10, pp. 711-724 (15 pages).
Butler, Jennifer E. et al., "The RNA Polymerase II Core Promoter: A Key Component in the Regulation of Gene Expression," Genes & Development (2002), vol. 16, pp. 2583-2592 (10 pages).
Cachon-Gonzalez, M. B. et al., "Effective Gene Therapy in an Authentic Model of Tay-Sachs-Related Diseases," Proc. Natl. Acad. Sci. (USA), vol. 103, No. 27 (Jul. 5, 2006), pp. 10373-10378 (6 pages).
Coloma, M. J. et al., "Transport Across the Primate Blood-Brain Barrier of a Genetically Engineered Chimeric Monoclonal Antibody to the Human Insulin Receptor," Pharmaceutical Research, vol. 17, No. 3 (2000), pp. 266-274 (9 pages).
Dayton, Robert D. et al., "The Advent of AAV9 Expands Applications for Brain and Spinal Cord Gene Delivery," Expert Opinion on Biological Therapy (2012), vol. 12, No. 6, pp. 757-766 (17 pages).
Deng, Wensheng et al., "TFIIB Recognition Elements Control the TFIIA-NC2 Axis in TYranscriptional Regulation," Molecular and Cell Biology (2009), vol. 29, No. 6, pp. 1389-1400 (12 pages).
Dobrenis, Kostantin et al., "Neuronal Lysosomal Enzyme Replacement Using Fragment C of Tetanus Toxin," Proc. Natl. Acad. Sic, USA, vol. 89 (Mar. 1992), pp. 2297-2301 (5 pages).
Dong, Biao et al., "Characterization of Genome Integrity for Oversized Recombinant AAV Vector," Molecular Therapy (2010), vol. 18, No. 1, pp. 87-92 (6 pages).
Duque, Sandra et al., "Intravenous Administration of Self-Complementary AAV9 Enables Transgene Delivery to Adult Motor Neurons," Molecular Therapy, vol. 17, No. 7 (Jul. 2009), pp. 1187-1196 (10 pages).
Even, Dan Y. et al., "Engineered Promoters for Potent Transient Overexpression," PLOS ONE (2016), 11(2), pp. 1-19 (19 pages).
Federici, T. et al., "Robust Spinal Motor Neuron Transduction Following Intrathecal Delivery of AAV9 in Pigs," Gene Therapy, vol. 19 (2012), pp. 852-859 (8 pages).
Fernandes, M. J. G. et al., "Identification of Candidate Active Site Residues in Lysosomal Beta-Hexosaminidase A*," J. Biol Chem., vol. 272, No. 2 pp. 814-820, ISSN 1083-351X (http://www.jbc.org/content/272/2/814.long) Jan. 10, 1997 (7 pages).
Fitzgerald, Peter C. et al., "Comparative Genomics of *Drosophila* and Human Core Promoters," Genome Biology (2006), vol. 7, Issue 7, Article R53, 22 pages.
Fitzsimons, Helen L. et al., "Promoters and Regulatory Elements that Improve Adeno-Associated Virus Transgene Expression in the Brain," Methods (2002), vol. 28, pp. 227-236 (10 pages).
Folch, Jordi et al., "A Simple Method for the Isolation and Purification of Total Lipides from Animal Tissues," J. Biol. Chem., vol. 226 (1957), pp. 497-509 (13 pages).
Foust, Kevin D. et al., "Intravascular AAV9 Preferentially Targets Neonatal Neurons and Adult Astrocytes," Nature Biotechnology (2009), vol. 27, No. 1, pp. 59-65 (7 pages).
Fu, Haiyan et al., "Self-Complementary Adeno-Associated Virus Serotype 2 Vector: Global Distribution and Broad Dispersion of AAV-Mediated Transgene Expression in Mouse Brain," Molecular Therapy (2003), vol. 8, No. 6, pp. 911-917 (7 pages).
Gabathuler, Reinhard "Approaches to Transport Therapeutic Drugs Across the Blood-Brain Barrier to Treat Brain Diseases," Neurobiology of Disease, vol. 37 (2010), pp. 48-57 (10 pages).
Gray, Steven J. "Gene Therapy and Neurodevelopmental Disorders," Neuropharmacology, vol. 68 (2013), pp. 136-142 (7 pages).
Gray, Steven J. et al., "Optimizing Promoters for Recombinant Adeno-Associated Virus-Mediated Gene Expression in the Peripheral and Central Nervous System Using Self-Complementary Vectors," Human Gene Therapy (2011), vol. 22, No. 9, pp. 1143-1153 (11 pages).
Gray, Steven J. et al., "Preclinical Differences of Intravascular AAV9 Delivery to Neurons and Glia: A Comparative Study of Adult Mice and Nonhuman Primates," Molecular Therapy, vol. 19, No. 6 (Jun. 2011), pp. 1058-1069 (12 pages).
Guidotti, J. E. et al., "Adenoviral Gene Therapy of the Tay-Sachs Disease in Hexosaminidase A-Deficient Knock-Out Mice," Human Molecular Genetics, vol. 8, No. 5 (1999) pp. 831-838 (8 pages).
Guo, Z. S. et al., "Gene Transfer: The Challenge of Regulated Gene Expression," Trends in Molecular Medicine (2008), vol. 14, No. 9, pp. 410-418 (9 pages).
Hou, Yongmin et al., "A Pro Ser Substitution in the Beta-Subunit of Beta-Hexosaminidase A Inhibits a-Subunit Hydrolysis of GM2 Ganglioside, Resulting in Chronic Sandhoff Disease," The Journal of Biological Chemistry, vol. 273, No. 33 (Aug. 14, 1998), pp. 21386-21392 (7 pages).
"International Search Report and Written Opinion," for PCT Application No. PCT/IB2015/001208, dated Dec. 4, 2015 (15 pages).
Juven-Gershon, Tamar et al., "Rational Design of a Super Core Promoter that Enhances Gene Expression," Nature Methods (2006), vol. 3, No. 11, pp. 917-922 (6 pages).
Juven-Gershon, Tamar et al., "Regulation of Gene Expression via the Core Promoter and the Basal Transcriptional Machinery," Developmental Biology (2010), vol. 339, pp. 225-229 (5 pages).
Juven-Gershon, Tamar et al., "The RNA Polymerase II Core Promoter—The Gateway to Transcription," Current Opinion in Cell Biology (2008), vol. 20, pp. 253-259 (7 pages).
Karumuthil-Melethil, Subha et al., "Novel Vector Design and Hexosaminidase Variant Enabling Self-Complementary AAV for the Treatment of Tay-Sachs Disease," Human Gene Therapy (2016), pp. 1-32 (32 pages).
Kuegler, S. et al., "Differential Transgene Expression in Brain Cells In Vivo and In Vitro from AAV-2 Vectors with Small Transcriptional Control Units," Virology (2003), vol. 311, No. 1, pp. 89-95 (7 pages).
Lacorazza, H. D. et al., "Expression of Human Beta-Hexosaminidase a-Subunit Gene (the Gene Defect of Tay-Sachs Disease) In Mouse Brains Upon Engraftment of Transduced Progenitor Cells," Nature Medicine, vol. 2, No. 4 (Apr. 1996), pp. 424-429 (6 pages).
Lemieux, M. J. et al., "Crystallographic Structure of Human Beta-Hexosaminidase A: Interpretation of Tay-Sachs Mutations and Loss of GM2 Ganglioside Hydrolysis," J. Mol. Biol., vol. 359 (2006) pp. 913-929 (17 pages).
Lim, Chin Y. et al., "The MTE, A New Core Promoter Element for Transcription by RNA Polymerase II," Genes & Development (2004), vol. 18, pp. 1606-1617 (12 pages).
Lukashchuk, Vera et al., "AAV9-Mediated Central Nervous System-Targeted Gene DeliveryVia Cisterna Magna Route in Mice," Molecular Therapy Methods & Clinical Development (2016), 3:15055, pp. 1-10 (10 pages).
Mahuran, Don J. "Characterization of Human Placental Beta-Hexosaminidase l2," The Journal of Biological Chemistry, vol. 265, No. 12 (Apr. 25, 1990), pp. 6794-6799 (8 pages).
Mahuran, Don J. et al., "The Biochemistry of HEXA and HEXB Gene Mutations Causing GM2 Gangliosidosis," Biochim Biophys Acta, vol. 1096 (1991), pp. 87-94 (8 pages).
Maier, Timm et al., "The X-Ray Crystal Structure of Human Beta-Hexosaminidase B Provides New Insights into Sandhoff Disease," J. Mol. Biol., vol. 328 (2003), pp. 669-681 (13 pages).
Mark, Brian L. et al., "Crystal Structure of Human Beta-Hexosaminidase B: Understanding the Molecular Basis of Sandhoff and Tay-Sachs Disease," J. Mol. Biol. vol. 327, (2003), pp. 1093-1109 (17 pages).
Martino, S. et al., "A Direct Gene Transfer Strategy Via Brain Internal Capsule Reverses the Biochemical Defect in Tay-Sachs Disease," Human Molecular Genetics, vol. 14, No. 15 (2005), pp. 2113-2123 (11 pages).
Maston, Glenn A. et al., "Transcriptional Regulatory Elements in the Human Genome," Annual Review of Genomics and Human Genetics (2006), vol. 7, pp. 29-59 (31 pages).
Matsuoka, K et al., "Therapeutic Potential of Intracerebroventricular Replacement of Modified Human Beta-Hexosaminidase B for GM2 Gangliosidosis.," Mol Ther. vol. 19,

(56) References Cited

OTHER PUBLICATIONS

No. 6, pp. 1017-1024, ISSN 1525-0024 (http://www.nature.com/mt/journal/v19/n6/full/mt201127a.html) Apr. 12, 2011 (8 pages).
Mccarty, D M. et al., "Adeno-Associated Virus Terminal Repeat (TR) Mutant Generates Self-Complementary Vecotrs to Overcome the Rate-Limiting Step to Transduction In Vivo," Gene Therapy (2003), vol. 10, No. 26, pp. 2112-2118 (7 pages).
Mccarty, D. M. et al., "Self-Complementary Recombinant Adeno-Associated Virus (scAAV) Vectors Promote Efficient Transduction Independently of DNA Synthesis," Gene Therapy (2001), vol. 8, No. 16, pp. 1248-1254 (7 pages).
Mccarty, Douglas M. et al., "Self-Complementary AAV Vectors; Advances and Applications," Molecular Therapy (2008), vol. 16, No. 10, pp. 1648-1656 (9 pages).
Mules, Emilie H. et al., "Six Novel Deleterious and Three Neutral Mutations in the Gene Encoding the a-Subunit of Hexosaminidase A in Non-Jewish Individuals," Am. J. Hem. Genet., vol. 50, (1992), pp. 834-841 (8 pages).
Nathanson, Jason L. et al., "Short Promoters in Viral Vectors Drive Selectivbe Expression in Mammalian Inhibitory Neurons, but Do Not Restrict Activity to Specific Inhibitory Cell-Types," Frontiers in Neural Circuits (2009), Volum3 3, Article 19, pp. 1-24 (24 pages).
Norflus, Francine et al., "Promoters for the Human Beta-Hexosaminidase Genes, HEXA and HEXB," DNA and Cell Biology (1996), vol. 15, No. 2, pp. 89-97 (10 pages).
Ohler, Uwe et al., "Computational Analysis of Core Promoters inthe *Drosophila* Genome," Genome Biology (2002), vol. 3, No. 12, pp. 1-12 (12 pages).
Osmon, Karlaina J. et al., "Systemic Gene Transfer of a Hexosaminidase Variant Using a scAAV9.47 Vector Corrects GM2 Gangliosidosis in Sandhoff Mice," Human Gene Therapy (2016), pp. 1-23 (23 pages).
Perry, Laura C. et al., "New Approaches to Prediction of Immune Responses to Therapeutic Proteins During Preclinical Development," Drugs R D, vol. 9, No. 6 (2008) pp. 385-396 (12 pages).
Samaranch, Lluis et al., "AAV9-Mediated Expression of a Non-Self Protein in Nonhuman Primate Central Nervous System Triggers Widespread Neuroinflammation Driven by Antigen-Presenting Cell Transduction," Molecular Therapy, vol. 22, No. 2 (Feb. 2014), pp. 329-337 (9 pages).
Sandelin, Albin et al., "Mammalian RNA Polymerase II Core Promoters: Insights from Genome-Wide Studies," Nature Reviews Genetics (2007), vol. 8, pp. 424-436 (13 pages).
Sands, Mark S. et al., "Gene Therapy for Lysosomal Storage Diseases," Molecular Therapy (2006), vol. 13, No. 5, pp. 839-849 (11 pages).
Schorpp, Marina et al., "The Human Ubiquitin C Promoter Directs High Ubiquitous Expression of Transgenese in Mice," Nucleic Acids Research (1996), vol. 24, No. 9, pp. 1787-1788 (2 pages).
Sharma, Rohita et al., "A Single Site in Human Beta-Hexosaminidase A Binds Both 6-Sulfate-Groups on Hexosamines and the Sialic Acid Moiety of GM2 Ganglioside," Biochim Biophys Acta, vol. 1637 (2003), pp. 113-118 (6 pages).
Sharma, Rohita et al., "Identification of the 6-Sulfate Binding Site Unique to a-Subunit-Containing Isozymes of Human Beta-Hexosaminidase," Biochemistry, vol. 40 (2001), pp. 5440-5446 (7 pages).
Shevtsova, Z. et al., "Promoters and Serotypes: Targeting of Adeno-Associated Virus Vectors for Gene Transfer in the Rat Central Nervous System In Vitro and In Vivo," Experimental Physiology (2005), 90 (1), pp. 53-59 (7 pages).
Sinici, I et al., "In Cellulo Examination of a Beta-Alpha Hybrid Construct of Beta-Hexosaminidase A Subunits, Reported to Interact with the GM2 Activator Protein and Hydrolyze GM2 Ganglioside," (http://journals.plos.org/plosone/article?id=10.1371/journal.pone. 0057908). vol. 8, No. 3, pp. 1-8, ISSN 1932-6203 Mar. 4, 2013 (8 pages).
Sinici, Incilay et al., "Comparison of HCMV IE and EF-1x Promoters for the Stable Expression of Beta-Subunit of Hexosaminidase in CHO Cell Lines," Biochemical Genetics (2006), vol. 44, Nos. 3/4, pp. 173-180 (8 pages).
Smiljanic-Georgijev, Natasha et al., "Characterization of the Affinity of the GM2 Activator Protein for Flycolipids by a Fluorescence Dequenching Assay," Biochim Biophys Acta, vol. 1339 (1997) pp. 192-202 (11 pages).
Spencer, Brian J. et al., "Targeted Delivery of Proteins Across the Blood-Brain Barrier," Proc Natl Acad Sci USA, vol. 104, No. 18 (May 1, 2007), pp. 7594-7599 (6 pages).
Theisen, Joshua W. et al., "Three Key Subregions Contribute to the Function of the Downstream RNA Polymerase II Core Promoter," Molecular and Cellular Biology (2010), vol. 30, No. 14, pp. 3471-3479 (9 pages).
Tornoe, Jens et al., "Generation of a Synthetic Mammalian Promoter Libraryby Modification of Sequences Spacing Transcription Factor Binding Sites," Gene (2002), vol. 297, pp. 21-32 (12 pages).
Tropak, Michael B. et al., "A Sensitive Fluorescence-Based Assay for Monitoring GM2 Ganglioside Hydrolysis in Live Patient Cells and Their Lysates," Glycobiology, vol. 20, No. 3 (2010), pp. 356-365 (10 pages).
Tropak, Michael B. et al., "Construction of a Hybrid β-Hexosaminidase Subunit Capable of Forming Stable Homodimers that Hydrolyze GM2 Ganglioside In Vivo," Molecular Therapy—Methods & Clinical Development 3, Article No. 15057 (2016), doi: 10.1038/mtm.2015.57 (15 pages).
Tropak, Michael B. et al., "Pharmacological Enhancement of Beta-Hexosaminidase Activity in Fibroblasts from Adult Tay-Sachs and Sandhoff Patients," The Journal of Biological Chemistry, vol. 279, No. 14 (Apr. 2, 2004), pp. 13478-13487 (10 pages).
Walia, Jagdeep S. et al., "Long-Term Correction of Sandhoff Disease Following Intravenous Delivery of rAAV9 to Mouse Neonates," Molecular Therapy (2015), vol. 23, No. 3, pp. 414-422 (9 pages).
Wang, C. Y. et al., "Improved Neuronal Transgene Expression from and AAV-2 Vector with a Hybrid CMV Enhancer/PDGF-Beta Promoter," The Journal of Gene Medicine (2005), vol. 7, pp. 945-955 (11 pages).
Wright, Christine S. et al., "Crystal Structure of Human GN2-Activator Protein with a Novel Beta-Cup Topology," J. Mol. Biol, vol. 304 (2000), pp. 411-422 (12 pages).
Wu, Zhijian et al., "Effect of Genome Size on AAV Vector Packaging," Molecular Therapy (2010), vol. 18, No. 1, pp. 80-86 (7 pages).
Yew, Nelson S. et al., "CpG-Depleted Plasmid DNA Vectors with Enhanced Safety and Long-Term Gene Expression In Vivo," Molecular Therapy (2002), vol. 5, No. 6, pp. 731-738 (8 pages).
"International Preliminary Report on Patentability," for PCT Application No. PCT/US2016/032496 dated Nov. 30, 2017 (8 pages).

\* cited by examiner

```
                                        TATA BOX              Inr                      MTE      DPE
                                           3       2      1           1                 2        3        4
                                        65432 10987654 32109876543210 1234567890123 4567 8901234567890123 456789012

Portion of JeT promoter:
ATGAT TATATAAG GACGGCCGGGTGTGGCACAG T AGTTCG GTCGCAGCCGG  CSARCSSAACGS (SEQ ID NO: 12)
       TATAWARR                       Y ANWYV                 PGWYV Example 1: Modified Portion JeT promoter with addition of MTE (without CpG) and DPE consensus sequence:
ATGAT TATATAAG GACGGCCGGGTGTGGCACAG T AGTTCG GTCGCAGCCGG GATTGGGTCGCGGTT CTTGTTTGT (SEQ ID NO: 13)

Example 2: Modified Portion JeT promoter with addition of MTE (without CpG) consensus sequence:
ATGAT TATATAAG GACGGCCGGGTGTGGCACAG T AGTTCG GTCGCAGCCGG CCAGCCCAACAGACG CTTGTTTGT (SEQ ID NO: 14)

Example 2: Modified Portion JeT promoter with addition of MTE and DPE consensus sequence:
ATGAT TATATAAG GACGGCCGGGTGTGGCACAG T AGTTCG GTCGCAGCCCT CGAGCCGAGCAGACG CTTGTTTGT (SEQ ID NO: 15)

Example 3: Modified Portion JeT promoter with addition of MTE and DPE consensus sequence:
ATGAT TATATAAG GACGGCCGGGTGTGGCACAG T AGTTCG GTCGCAGCCCT CGAACAGAACACAGACG CTTGTTTGT (SEQ ID NO: 16)
```

POLYNUCLEOTIDES, VECTORS AND METHODS FOR INSERTION AND EXPRESSION OF TRANSGENES

This application claims the benefit of U.S. Provisional Application No. 62/162,199, filed May 15, 2015, the content of which is herein incorporated by reference in its entirety.

REFERENCE TO SEQUENCE LISTING

This application is being filed electronically via EFS-Web and includes an electronically submitted sequence listing in .txt format. The .txt file contains a sequence listing entitled "seqlisting_ST25.txt" created on May 3, 2016, and having a size of 32 KB. The sequence listing contained in this .txt file is part of the specification and is incorporated herein by reference in its entirety.

FIELD

Embodiments herein relate to polynucleotides, vectors and methods for the insertion and expression of transgenes.

BACKGROUND

Genetic disorders, such as those caused by the absence of, or a defect in, a desirable gene (loss of function) or expression of an undesirable or defective gene or (gain of function), can lead to a variety of disease states.

As an example, GM2 gangliosidosis is a family of three genetic neurodegenerative disorders caused by the accumulation of GM2 gangliosides (GM2). Two of these are due to the deficiency of one of 2 similar but non-identical subunits that comprise heterodimeric β-hexosaminidase A (HexA) which hydrolyzes GM2. Mutations in the α-subunit (encoded by HEXA) of the enzyme HexA lead to Tay-Sachs disease (TSD), wherein mutations in the β-subunit (encoded by HEXB) lead to Sandhoff disease (SD). In these diseases, the malfunctioning protein is unable to play its role in cleaving GM2 ganglioside, whose accumulation within the neurons of the central nervous system is ultimately toxic. The resulting neuronal death induces the primary symptoms of the disease including motor impairment, seizures, and sensory impairments.

Depending on the specific condition, approaches to treating genetic disorder diseases can include dietary changes or replacement of the particular enzyme that is missing. For some conditions, limiting certain substances in the diet can help prevent the buildup of potentially toxic substances that are normally broken down by the missing or defective enzyme. In some cases, enzyme replacement therapy can help compensate for the enzyme shortage. However, diet modification only works for some diseases. Intravenous enzyme replacement therapy generally requires repeated infusions and does not adequately distribute to all tissues requiring enzyme enhancement such as, for some lysosomal diseases, the central nervous system ("CNS").

A newer approach to treating such diseases is gene transfer based therapy wherein a transgene that can ameliorate the symptoms of the disease is inserted into the genetic material of the patient. For diseases that are caused by the expression of a deleterious protein, such as Huntington's disease or myotonic dystrophy, gene transfer based therapy could potentially also be used wherein a transgene codes for a polynucleotide that could decrease the expression of the deleterious protein or RNA and ameliorate the symptoms of the disease.

SUMMARY

Embodiments herein include polynucleotides, vectors and methods for the insertion and expression of transgenes. In an embodiment, a polynucleotide is included. The polynucleotide can include a JeT promoter or variant thereof, an intron sequence less than 400 bases in length, and a polynucleotide sequence encoding a polypeptide or protein operatively linked to the promoter.

In an embodiment, a recombinant vector is included. The recombinant vector can include a JeT promoter or variant thereof, an intron sequence less than 400 bases in length, and a polynucleotide sequence encoding a polypeptide or protein operatively linked to the promoter.

In an embodiment, a transgene expression system is included. The transgene expression system can include a plasmid comprising DNA encoding a transcription unit comprising a transgene operably linked to a JeT promoter and an intron sequence of less than 400 bases in length.

In an embodiment, a method of treating a mammal for a lysosomal storage disease is included. The method can include providing an adeno-associated virus (AAV) vector, the vector comprising a heterologous polynucleotide encoding a β-hexosaminidase protein, a subunit thereof, or a variant thereof, wherein the heterologous polynucleotide sequence is operably linked to a JeT promoter and an intron sequence less than 400 bases in length; and administering an amount of the AAV vector to the mammal wherein the β-hexosaminidase protein, subunit thereof, or variant thereof is expressed in the mammal.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which:

FIG. 7 shows modifications of a JeT promoter in accordance with various embodiments herein.

Figure 1:
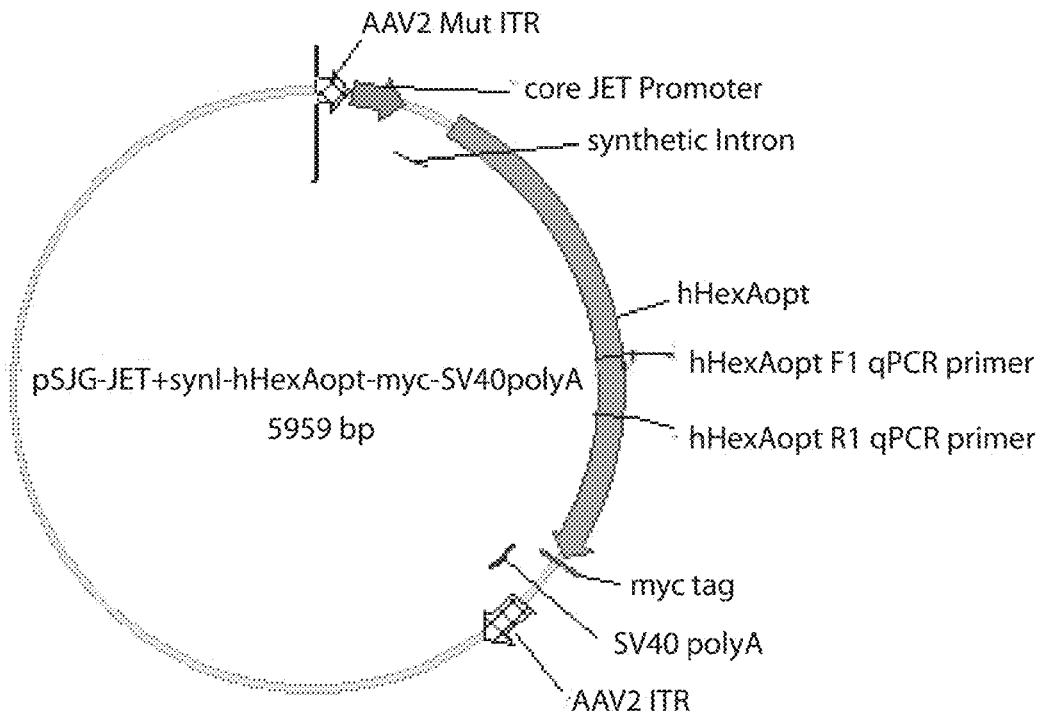
FIG. 1 is a diagram of an exemplary vector plasmid in accordance with various embodiments herein.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

The embodiments described herein are not intended to be exhaustive or to limit the invention to the precise forms disclosed in the following detailed description. Rather, the embodiments are chosen and described so that others skilled in the art can appreciate and understand the principles and practices.

As described above, a newer approach to treating genetic disorders is gene transfer based therapy. Adeno-associated virus (AAV) vectors are useful for gene transfer based therapy. However, the DNA packaging limitation of AAV imposes a major constraint on the genetic engineering of an AAV vector. Recent studies have demonstrated that the production yield of AAV vectors is significantly reduced when the DNA size is increased above the wild-type genome length (approximately 4.7 kilobases, kb). For a large transgene, this size limitation is a substantial constraint in the design of an AAV vector. The HEXA gene, has a length of 1590 nucleotides, and therefore its length places constraints on AAV vector design. Because of the limited DNA packaging in AAV, the regulatory sequence needs to be very short.

It has been generally observed that the use of AAV vectors already containing dual-strand DNA, also called self-complementary AAV or scAAV, provides significantly greater transduction efficiency than AAV vectors utilizing ssDNA. As such, it is desirable for the vector to be self-complementary. The major disadvantage of using scDNA in an AAV construct is that it that the maximum length of the therapeutic gene is reduced by approximately half because of the need to include its complementary sequence. For example, the ssAAV vector sequence length, minus the two 145 nucleotide ITRs, is limited to approximately 4.4 kb. This 4.4 kb DNA sequence length must include the transgene, the associated promoter/intron, and a polyadenylation tail (pA). When using self-complementary constructs, this same 4.4 kb limit must include the transgene and its complementary sequence, the promoter/intron and its complement, the pA and its complement, and an additional ITR. Considering this extra ITR has a length of approximately 0.1 kb, the total sequence length of the transgene, promoter/intron, and pA must be kept shorter than approximately 2.15 kb. Therefore, using a 1.6 kb transgene, the promoter/intron and the pA must have a total sequence length of less than only 0.55 kb in order to keep the total DNA sequence length less than the wildtype AAV DNA sequence length of 4.7 kb.

In addition, the use of an intron in combination with the JeT promoter can improve the expression level over what might be achieved without such an intron. While the degree of expression level improvement can, in some instances, vary with the length of the intron, relatively short intron sequences can be desirable because of sufficient improvements to expression levels while still being consistent with size constraints associated with certain vectors such as those discussed above.

In an embodiment, a self-complimentary polynucleotide is included having a JeT promoter or variant thereof, an intron sequence less than 400 bases in length, and a polynucleotide sequence encoding a polypeptide or protein operatively linked to the promoter.

As used term, the term "operable linkage" or "operably linked" refers to a physical or functional juxtaposition of the components so described as to permit them to function in their intended manner. In the example of an expression control element in operable linkage with a polynucleotide, the relationship is such that the control element modulates expression of the nucleic acid. More specifically, for example, two DNA sequences operably linked means that the two DNAs are arranged (cis or trans) in such a relationship that at least one of the DNA sequences is able to exert a physiological effect upon the other sequence.

The term "isolated," when used as a modifier of a composition, means that the compositions are made by the hand of man or are separated, completely or at least in part, from their naturally occurring in vivo environment. Generally, isolated compositions are substantially free of one or more materials with which they normally associate with in nature, for example, one or more protein, nucleic acid, lipid, carbohydrate, cell membrane. The term "isolated" does not exclude alternative physical forms of the composition, such as fusions/chimeras, multimers/oligomers, modifications (e.g., phosphorylation, glycosylation, lipidation) or derivatized forms, or forms expressed in host cells produced by the hand of man.

The terms "polynucleotide" and "nucleic acid" are used interchangeably herein to refer to all forms of nucleic acid, oligonucleotides, including deoxyribonucleic acid (DNA) and ribonucleic acid (RNA). Polynucleotides include genomic DNA, cDNA and anti sense DNA, and spliced or unspliced mRNA, rRNA, tRNA and inhibitory DNA or RNA (RNAi, e.g., small or short hairpin (sh)RNA, microRNA, small or short interfering (si)RNA, trans-splicing RNA, or antisense RNA). Polynucleotides include naturally occurring, synthetic, and intentionally altered or modified polynucleotides as well as analogues and derivatives. Polynucleotides can be single, double, or triplex, linear or circular, and can be of any length.

A "heterologous" polynucleotide, as an example, can refer to a polynucleotide inserted into a vector for purposes of vector-mediated transfer/delivery of the polynucleotide into a cell. Heterologous polynucleotides are typically distinct from nucleic acid specific to the vector itself. Once transferred/delivered into the cell, a heterologous polynucleotide, can be expressed (e.g., transcribed, and translated if appropriate).

The "polypeptides", "proteins" and "peptides" encoded by the "polynucleotide sequences," can include full-length native sequences, as with naturally occurring proteins, as well as functional subsequences, modified forms or sequence variants so long as the subsequence, modified form or variant retains some degree of the desired functionality, such as the functionality of the full-length protein.

Polynucleotides, polypeptides and subsequences thereof can include modified and variant forms. As used herein, the terms "modify" or "variant" and grammatical variations thereof, mean that a polynucleotide, polypeptide or subsequence thereof deviates from a reference sequence. Aspects herein include naturally and non-naturally occurring variants. Modified and variant sequences may have substantially the same, greater or less activity or function than a reference sequence, but can at least retain partial activity or function of the reference sequence.

Non-limiting examples of modifications include one or more amino acid substitutions (e.g., 1-3, 3-5, 5-10, 10-15, 15-20, 20-25, 25-30, 30-40, 40-50, or more residues), additions (e.g., insertions or 1-3, 3-5, 5-10, 10-15, 15-20, 20-25, 25-30, 30-40, 40-50, or more residues) and deletions (e.g., subsequences or fragments) of a reference sequence. In particular embodiments, a modified or variant sequence retains at least part of a function or an activity of unmodified sequence. Such modified forms and variants can have less than, the same, or greater, but at least a part of, a function or activity of a reference sequence, for example, as described herein.

A variant can have one or more non-conservative or conservative amino acid sequence differences or modifications, or both. A "conservative substitution" is the replacement of one amino acid by a biologically, chemically or structurally similar residue. Biologically similar means that the substitution does not destroy a biological activity. Structurally similar means that the amino acids have side chains with similar length, such as alanine, glycine and serine, or a similar size. Chemical similarity means that the residues have the same charge or are both hydrophilic or hydrophobic. Particular examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, and the like. Particular examples of conservative substitutions include the substitution of a hydrophobic residue such as isoleucine, valine, leucine or methionine for another, the substitution of a polar residue for another, such as the substitution of arginine for lysine, glutamic for aspartic acids, or glutamine for asparagine, and the like. For example, conservative amino acid substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. A "conservative substitution" also includes the use of a substituted amino acid in place of an unsubstituted parent amino acid.

Aspects herein can include gene and protein variants (e.g., of polynucleotides encoding proteins described herein) that retain one or more biological activities (e.g., hydrolyzing GM2 gangliosides, either alone or in combination with other proteins). Such variants of proteins or polypeptides include proteins or polypeptides which have been or may be modified using recombinant DNA technology such that the protein or polypeptide possesses altered or additional properties, for example, variants conferring enhanced protein stability in plasma or enhanced activity of the protein. Variants can differ from a reference sequence, such as naturally occurring polynucleotides, proteins or peptides.

At the nucleotide sequence level, a naturally and non-naturally occurring variant gene will typically be at least about 50% identical, more typically about 70% identical, even more typically about 80% identical (90% or more identity) to the reference gene. At the amino acid sequence level, a naturally and non-naturally occurring variant protein will typically be at least about 70% identical, more typically about 80% identical, even more typically about 90% or more identity to the reference protein, although substantial regions of non-identity are permitted in non-conserved regions (e.g., less, than 70% identical, such as less than 60%, 50% or even 40%). In other embodiments, the sequences have at least 60%, 70%, 75% or more identity (e.g., 80%, 85% 90%, 95%, 96%, 97%, 98%, 99% or more identity) to a reference sequence. Procedures for the introduction of nucleotide and amino acid changes in a polynucleotide, protein or polypeptide are known to the skilled artisan (see, e.g., Sambrook et al, (1989)).

The term "identity," "homology" and grammatical variations thereof, mean that two or more referenced entities are the same, when they are "aligned" sequences. Thus, by way of example, when two polypeptide sequences are identical, they have the same amino acid sequence, at least within the referenced region or portion. Where two polynucleotide sequences are identical, they have the same polynucleotide sequence, at least within the referenced region or portion. The identity can be over a defined area (region or domain) of the sequence. An "area" or "region" of identity refers to a portion of two or more referenced entities that are the same. Thus, where two protein or nucleic acid sequences are identical over one or more sequence areas or regions they share identity within that region. An "aligned" sequence refers to multiple polynucleotide or protein (amino acid) sequences, often containing corrections for missing or additional bases or amino acids (gaps) as compared to a reference sequence.

The identity can extend over the entire sequence length or a portion of the sequence. In particular aspects, the length of the sequence sharing the percent identity is 2, 3, 4, 5 or more contiguous polynucleotide or amino acids, e.g., 6, 7, 8, 9, 10, 11, 12, 13, 14, 15, 16, 17, 18, 19, 20, etc. contiguous amino acids. In additional particular aspects, the length of the sequence sharing identity is 20 or more contiguous polynucleotide or amino acids, e.g., 20, 21, 22, 23, 24, 25, 26, 27, 28, 29, 30, 31, 32, 33, 34, 35, etc. contiguous amino acids. In further particular aspects, the length of the sequence sharing identity is 35 or more contiguous polynucleotide or amino acids, e.g., 35, 36, 37, 38, 39, 40, 41, 42, 43, 44, 45, 45, 47, 48, 49, 50, etc., contiguous amino acids. In yet further particular aspects, the length of the sequence sharing identity is 50 or more contiguous polynucleotide or amino acids, e.g., 50-55, 55-60, 60-65, 65-70, 70-75, 75-80, 80-85, 85-90, 90-95, 95-100, 100-110, etc. contiguous polynucleotide or amino acids.

The terms "homologous" or "homology" mean that two or more referenced entities share at least partial identity over a given region or portion. "Areas, regions or domains" of homology or identity mean that a portion of two or more referenced entities share homology or are the same. Thus, where two sequences are identical over one or more sequence regions they share identity in these regions. "Substantial homology" means that a molecule is structurally or functionally conserved such that it has or is predicted to have at least partial structure or function of one or more of the structures or functions (e.g., a biological function or activity) of the reference molecule, or relevant/corresponding region or portion of the reference molecule to which it shares homology.

The extent of identity (homology) between two sequences can be ascertained using a computer program and mathematical algorithm. Such algorithms that calculate percent sequence identity (homology) generally account for sequence gaps and mismatches over the comparison region or area. For example, a BLAST (e.g., BLAST 2.0) search algorithm (see, e.g., Altschul et al., J. Mol. Biol. 215:403 (1990), publicly available through NCBI) has exemplary search parameters as follows: Mismatch −2; gap open 5; gap extension 2. For polypeptide sequence comparisons, a BLASTP algorithm is typically used in combination with a scoring matrix, such as PAM 100, PAM 250, BLOSUM 62 or BLOSUM 50. FASTA (e.g., FASTA2 and FASTA3) and SSEARCH sequence comparison programs are also used to quantitate extent of identity (Pearson et al., Proc. Natl. Acad. Sci. USA 85:2444 (1988); Pearson, Methods Mol. Biol. 132:185 (2000); and Smith et al., J. Mol. Biol. 147: 195 (1981)). Programs for quantitating protein structural similarity using Delaunay-based topological mapping have also been developed (Bostick et al., Biochem Biophys Res Commun. 304:320 (2003)).

As used herein, the term "recombinant," such as in the context of recombinant polynucleotides and polypeptides, means that the compositions have been manipulated (i.e., engineered) in a fashion that generally does not occur in nature. For example, a recombinant AAV vector would be where a polynucleotide that is not normally present in the wild-type AAV is within the AAV particle and/or genome. For example, a particular example of a recombinant polynucleotide would be where a polynucleotide (e.g., gene) encoding a protein is cloned into a vector, with or without 5', 3' and/or intron regions that the gene is normally or not normally associated within the AAV genome.

The term "transgene" refers to a heterologous polynucleotide sequence that has been introduced into a cell or organism. Transgenes can include any polynucleotide, such as a gene that encodes a polypeptide or protein, a polynucleotide that is transcribed into an inhibitory polynucleotide, or a polynucleotide that is not transcribed (e.g., lacks an expression control element, such as a promoter that drives transcription). A cell or progeny thereof into which the transgene has been introduced is referred to as a "transformed cell", "transduced cell", or "transformant." In some cases, a transgene is included in progeny of the transformant or becomes a part of the organism that develops from the cell. Accordingly, in some cases, a "transformed", "transduced" or "transfected" cell (e.g., in a mammal, such as a cell or tissue or organ cell), means a genetic change in a cell following incorporation of an exogenous molecule, for example, a polynucleotide or protein (e.g., a transgene) into the cell. Thus, a "transfected", "transduced" or "transformed" cell is a cell, or progeny thereof, into which an exogenous molecule has been introduced, for example.

Particular non-limiting examples of polynucleotides encoding gene products (proteins) which are useful in accordance with the invention include, but are not limited to: genes that comprise or encode β-hexosaminidase proteins, or subunits thereof, or variants thereof, that are useful for hydrolyzing GM2 ganglioside. By way of example, polynucleotides herein can encode Hex B, a homodimer of β-subunits (encoded by the HEXB gene), or portions or variants thereof, Hex A, a heterodimer composed of a β and an α (encoded by the HEXA gene) subunit, or portions or variants thereof; GM2-activator protein (GM2AP), or portions or variants thereof, or the like. In some embodiments, the polynucleotide encoding a polypeptide or protein can code for a polypeptide having the sequence of residues 89-529 of the α-subunit of Hex A (SEQ ID NO: 9) or conservative variants thereof, or can code for a polypeptide having at least 70%, 75%, 80%, 85%, 90%, 95%, 98%, or 99% sequence identity to residues 89-529 of the α-subunit of Hex A (SEQ ID NO: 9) or conservative variants thereof.

Vectors:

Polynucleotide sequences in accordance with the invention can be inserted into a vector. The term "vector" refers to a plasmid, virus (e.g., AAV) or other vehicle that can be manipulated by insertion or incorporation of a polynucleotide. Such vectors can be used for genetic manipulation (i.e., "cloning vectors"), to introduce/transfer polynucleotides into cells, and to transcribe or translate the inserted polynucleotide in cells. A vector generally contains at least an origin of replication for propagation in a cell and expression control element(s) (e.g., a promoter). Control elements, including expression control elements such as promoters and enhancers, can be included within a vector to facilitate proper transcription and/or appropriate translation. Exemplary promoters are described in greater detail below.

Expression control can be effected at the level of transcription, translation, splicing, message stability, etc. Typically, an expression control element that modulates transcription is juxtaposed near the 5' end of the transcribed polynucleotide (i.e., "upstream"). Expression control elements can also be located at the 3' end of the transcribed sequence (i.e., "downstream") or within the transcript (e.g., in an intron). Expression control elements can be located at a distance away from the transcribed sequence (e.g., 100 to 500, 500 to 1000, 2000 to 5000, 5000 to 10,000 or more nucleotides from the polynucleotide), even at considerable distances. Nevertheless, owing to the polynucleotide length limitations, for AAV vectors, such expression control elements will typically be within 1 to 1000 nucleotides from the polynucleotide.

Functionally, expression of the operably linked polynucleotide is at least in part controllable by the element (e.g., promoter) such that the element modulates transcription of the polynucleotide and, as appropriate, translation of the transcript. A specific example of an expression control element is a promoter, which is usually located 5' of the transcribed sequence. Another example of an expression control element is an enhancer, which can be located 5', 3' of the transcribed sequence, or within the transcribed sequence.

Many different viral vectors can be used. Viral vectors can include retroviruses, adenoviruses, herpes simplex virus, lentiviruses, and the like.

Adeno-associated virus (AAV) vectors are a particular type of vector for the delivery of genes in vivo. As used herein, the term "serotype" is a distinction used to refer to an AAV having a capsid that is serologically distinct from other AAV serotypes. Serologic distinctiveness is determined on the basis of the lack of cross-reactivity between antibodies to one AAV as compared to another AAV. Such cross-reactivity differences are usually due to differences in capsid protein sequences/antigenic determinants (e.g., due to VP1, VP2, and/or VP3 sequence differences of AAV serotypes). AAV serotype can include AAV1, AAV2. AAV3. AAV4, AAV5, AAV6, AAV7, AAV 8. AAV9, AAV10 or AAV11. In some embodiments, the AAV serotype is selected from 1, 2, 4, 5, 7, 8, 9, and Rh10, which have been shown to be effective in central nervous system (CNS) applications.

AAV vectors can be constructed using recombinant techniques that are known to the skilled artisan, to include one or more heterologous polynucleotide sequences flanked with functional AAV ITRs. Incorporation of a heterologous polynucleotide defines the AAV as a recombinant vector, or an "rAAV vector." Such vectors can have one or more of the wild type AAV genes deleted in whole or in part, for example, a rep and/or cap gene, but retain at least one functional flanking ITR sequence, as necessary for the rescue, replication, and packaging of the AAV particle. Thus, an AAV vector includes sequences required in cis for viral replication and packaging (e.g., functional ITRs).

Vectors including AAV vectors of the invention can include still additional nucleic acid elements. These elements include, without limitation one or more copies of an AAV ITR sequence, a promoter/enhancer element, a transcription termination signal, 5' or 3' untranslated regions (e.g., polyadenylation sequences) which flank a polynucleotide sequence, or all or a portion of an intron. Such elements also optionally include a transcription termination signal. A particular non-limiting example of a transcription termination signal is the SV40 transcription termination signal.

Promoter:

Various promoters can be used with embodiments herein. Based on size constraints associated with the AAV vector discussed above, it can be advantageous to pick a relatively small promoter. In some embodiments, the promoter is selected from the group consisting of RSV (329 bp), JeT (200 bp), and hUbC (397 bp) promoters. In various embodiments, the JeT promoter is used. The JeT promoter is a recombinant promoter with transcriptional activity comparable to a number of strong mammalian promoters. The JeT promoter takes advantage of a unique combination of transcription factor binding sites resulting in transcriptional activity comparable to a number of strong mammalian promoters such as the simian virus 40 (SV40) and ubiquitin (UbC) promoters. The promoter consists of five key elements: (1) a TATA box (TATATAA); (2) a transcription initiation site (Inr) (CTAGTTC); (3) a CAT consensus sequence (CCAAT) in conjunction with (4) a CArG element (CCTTTTATGG) and finally, (5) four Sp1 transcription binding sites (GGGCGG) arranged in two tandems. The CAT/CArG complex is also referred to as a Serum Response Element (SRE). Aspects of the JeT promoter are described in U.S. Pat. No. 6,555,674, the content of which is herein incorporated by reference.

The JeT promoter (SEQ ID NO: 1) or (SEQ ID NO: 2) takes advantage of a unique combination of transcription factor binding sites resulting in transcriptional activity comparable to a number of strong mammalian promoters such as the simian virus 40 (SV40) and ubiquitin (UbC) promoters. The promoter consists of five key elements: (1) a TATA box (TATATAA), (2) a transcription initiation site (Inr) (CTAGTTC), (3) a CAT consensus sequence (CCAAT) in conjunction with (4) a CArG element (CCTTTTATGG) (SEQ ID NO: 3) and finally, (5) four Sp1 transcription binding sites (GGGCGG) arranged in two tandems. The standard JeT promoter sequence is shown below:

A standard JeT promoter uses only transcription binding sites located upstream from the RNA Polymerase II initiation site (Inr). However, the inclusion of transcription factor binding elements downstream from the Inr can have a significant beneficial effect on the expression strength of a promoter. For example, the downstream promoter element (DPE) is often located from +28 to +32 (+33) and has a consensus of RGWYV(T) (using the IUPAC nucleotide code). The transcription factor II D (TFIID) binds cooperatively to the Inr and the DPE motifs.

A core downstream promoter element can also exist from +18 to +29 of the Inr initiation site, named the Motif Ten Element (MTE). The MTE has a role in binding the TFIID to the promoter. The MTE has a consensus sequence of CSARCSSAACGS (SEQ ID NO: 12) (using the IUPAC nucleotide code). See Lim C Y, Santoso B, Boulay T, Dong E, Ohler U, Kadonaga J T: The MTE, a new core promoter element for transcription by RNA polymerase II. *Genes Dev* 2004, 18(13):1606-1617.

In various embodiments herein, the JeT plus short intron promoter can be enhanced by substituting the JeT promoter sequence from +18 to +27 and from +28 to +33 from Inr A+1 with the consensus sequences of both MTE and DPE while minimizing CpG dinucleotides. This is illustrated in FIG. 7, which shows the promoter sequences from −36 to +42 relative to the transcription start site (Inr) for several examples of modified portions of JeT promoter sequences that can be used in embodiments. As such, in various embodiments herein a JeT promoter variant is included including the consensus sequences of the DPE or of both MTE and DPE.

An example is shown below (SEQ ID NO: 10) of a complete JeT Promoter sequence with the addition of a MTE/DPE consensus sequence and all CpG dinucleotides outside of the defined transcription factor binding elements replaced with CpA to avoid cytosine methylation. This sequence has 87% identity with SEQ ID NO: 1.

```
JeT promoter 195 bases
                                                       (SEQ ID NO: 1)
    1 GAATTCGGGC GGAGTTAGGG CGGAGCCAAT CAGCGTGCGC CGTTCCGAAA       50

51 GTTGCCTTTT ATGGCTGGGC GGAGAATGGG CGGTGAACGC CGATGATTAT      100

101 ATAAGGACGC GCCGGGTGTG GCACAGCTAG TTCCGTCGCA GCCGGGATTT      150

151 GGGTCGCGGT TCTTGTTTGT GGATCCCTGT GATCGTCACT TGACA           195

Another version of the JeT promoter is shown below:
JeT promoter 192 bases
                                                       (SEQ ID NO: 2)
    1 GAATTCGGGC GGAGTTAGGG CGGAGCCAAT CAGCGTGCGC CGTTCCGAAA       50

51 GTTGCCTTTT ATGGCTGGGC GGAGAATGGG CGGTGAACGC CGATGATTAT      100

101 ATAAGGACGC GCCGGGTGTG GCACAGCTAG TTCCGTCGCA GCCGGGATTT      150

151 GGGTCGCGGT TCTTGTTTGT GGATCCCTGT GATCGTCACT TG              192

Yet another version of the JeT promoter is shown below:
JET promoter 187 bases
                                                       (SEQ ID NO: 8)
    1 CGGGCGGAGT TAGGGCGGAG CCAATCAGCG TGCGCCGTTC CGAAAGTTGC       50

51 CTTTTATGGC TGGGCGGAGA ATGGGCGGTG AACGCCGATG ATTATATAAG      100

101 GACGCGCCGG GTGTGGCACA GCTAGTTCCG TCGCAGCCGG GATTTGGGTC      150

151 GCGGTTCTTG TTTGTGGATC CCTGTGATCG TCACTTG                    187
```

```
Modified JET promoter 195 bases
                                                         (SEQ ID NO: 10)
    1 GAATTCGGGC GGAGTTAGGG CGGAGCCAAT CAGCATGCAC CATTCCAAAA       50

51 GTTGCCTTTT ATGGCTGGGC GGAGAATGGG CGGTGAACAC CAATGATTAT      100

101 ATAAGGACAC ACCAGGTGTG GCACAGCTAG TTCCATCACA GCCAGCCAGC      150

151 CCAACAGACG TCTTGTTTGT GGATCCCTGT GATCATCACT TGACA           195
```

In various embodiments, promoter CpG dinucleotides can be replaced. CpG dinucleotides within a promoter can undergo cytosine methylation, and over time, result in a diminished expression of the associated transgene. To avoid this impact on the gene expression, CpG dinucleotides, which are not specifically within a consensus transcription binding site element, can be changed to CpA. These changes are intended to improve the long-term expression from the promoter-intron. Other alternative promoter sequences, such as where the CpG dinucleotides are changed to TpG, are also included herein. As such, in various embodiments, one or more CpG dinucleotides, that are not within a consensus transcription binding site element, are modified to reduce or eliminate the number of CpG dinucleotides. In some embodiments, all CpG dinucleotides within the promoter, that are not within a consensus transcription binding site element, are modified to reduce or eliminate the number of CpG dinucleotides.

In some embodiments, an alternative form of MTE can be used having two CpG dinucleotides in the consensus sequence. For example, alternative forms of MTE located at +18 to +27 from the Inr A+1 transcription initiation site can include CGAGCCGAGC (SEQ ID NO: 17) or CGAAC-CGAAC (SEQ ID NO: 18). In some embodiments, nucleotides CT can be included at locations +16 and +17 from the Inr A+1. In various embodiments, the JeT promoter sequence from −36 to +42 relative to the transcription start site (Inr) can be as shown in SEQ ID NOS: 13, 14, 15, or 16 of FIG. 7, or having 80%, 85%, 90%, 95%, 98% or 99% sequence identity thereto.

Following transcription of mRNA, the AUG codon indicates a translation initiation site that results in the first methionine amino acid of the expressed protein. The inclusion of ATG sequences within the promoter-intron that occurs following the transcription initiation site and before the intended translation initiation site can result in the translation of unintended amino acids and reduce the expression level of the intended protein. To prevent this occurrence, one or more (or all) of the in-frame or out-of-frame ATG sequences can be been modified. By way of example, "ATG" sequences can be changed to "ATA". Alternately, the "ATG" sequences can be changed to "GTG" or a combination of "ATA" and "GTG" or other triplets changes from "ATG". In various embodiments, those changes avoid and/or do not result in incorporating a CpG dinucleotide, per the potential issues with cytosine methylation discussed above.

In some embodiments, the intron element can be modified to enhance the expression level of the intended protein. By way of example, in some embodiments, in-frame and out-of-frame ATG start sites can be changed to ATA, for example, to avoid unintended initiation of translation prior to the transgene first methionine. In some embodiments, one or more in-frame and out-of-frame ATG start sites are changed to alternative nucleotides. In some embodiments, all in-frame and out-of-frame ATG start sites are changed to alternative nucleotides. An exemplary synthetic sequence (SEQ ID NO: 11) wherein in-frame and out-of-frame ATG start sites are replaced is as follows (this has 97% identity with SEQ ID NO: 4):

```
Synthetic Intron 140 bases
                                                         (SEQ ID NO: 11)
    1 GTAAGTCACT GACTGTCTAT ACCTGGGAAA GGGTGGGCAG GAGATAGGGC       50

51 AGTGCAGGAA AAGTGGCACT ATAAACCCTG CAGCCCTAGG AATACATCTA      100

101 GACAATTGTA CTAACCTTCT TCTCTTTCCT CTCCTGACAG                 140
```

In some embodiments, the promoter used with embodiments herein can have at least 60%, 65%, 70%, 75%, 80%, 85%, 90%, 95%, or 98% sequence identity with SEQ ID NO: 1, 2, 8, or 10, while being non-naturally occurring.

Intron:

Inclusion of an intron element can enhance expression compared with expression in the absence of the intron element. The intron can be synthetic. An exemplary synthetic intron sequence is as follows:

In some embodiments, the intron can be 800 bases or less in length. In some embodiments, the intron can be 750 bases or less, 700 bases or less, 650 bases or less, 600 bases or less, 550 bases or less, 500 bases or less, 450 bases or less, 400 bases or less, 350 bases or less, 300 bases or less, 250 bases or less, 200 bases or less, or 150 bases or less in length.

In some embodiments, the intron used with embodiments herein can have at least 60%, 65%, 70%, 75%, 80%, 85%, 90%, 95%, or 98% sequence identity with SEQ ID NO: 4 or 11, while being non-naturally occurring.

```
Synthetic intron 140 bases
                                                         (SEQ ID NO: 4)
    1 GTAAGTCACT GACTGTCTAT GCCTGGGAAA GGGTGGGCAG GAGATGGGGC       50

51 AGTGCAGGAA AAGTGGCACT ATGAACCCTG CAGCCCTAGG AATGCATCTA      100

101 GACAATTGTA CTAACCTTCT TCTCTTTCCT CTCCTGACAG                 140
```

The intron can be in various positions with respect to other components of the polynucleotide such as the promoter. In some embodiments, the promoter precedes the intron. However, in other embodiments, the intron can be contained in its entirety within the promoter. In some embodiments, the intron can also be in the 3' poly A segment. In some embodiments, the intron can be within the coding sequence (e.g., portion coding for polypeptide or protein) of the gene.

Methods:

Methods herein can include treatment methods. In various embodiments, methods herein further include inhibiting, decreasing or reducing one or more adverse (e.g., physical) symptoms, disorders, illnesses, diseases or complications caused by or associated with the disease. In various embodiments, a method of treating a mammal for a lysosomal storage disease is included. The method can include providing an adeno-associated virus (AAV) vector, the vector comprising a heterologous polynucleotide encoding a β-hexosaminidase protein, a subunit thereof, or a variant thereof. The heterologous polynucleotide sequence can be operably linked to a JeT promoter, or a variation thereof, and an intron sequence less than 400 bases in length. The method can also include administering an amount of the AAV vector to the mammal wherein the β-hexosaminidase protein, subunit thereof, or variant thereof is expressed in the mammal.

Compositions, methods and uses of the invention, can be administered in a sufficient or effective amount to a subject in need thereof. An "effective amount" or "sufficient amount" refers to an amount that provides, in single or multiple doses, alone or in combination, with one or more other compositions (therapeutic agents such as a drug), treatments, protocols, or therapeutic regimens agents, a detectable response of any duration of time (long or short term), an expected or desired outcome in or a benefit to a subject of any measurable or detectable degree or for any duration of time (e.g., for minutes, hours, days, months, years, or cured).

In some embodiments, a method of making a polynucleotide and/or vector is included herein. Polynucleotides and polypeptides including modified forms can be made using various standard cloning, recombinant DNA technology, via cell expression or in vitro translation and chemical synthesis techniques. Purity of polynucleotides can be determined through sequencing, gel electrophoresis and the like. For example, nucleic acids can be isolated using hybridization or computer-based database screening techniques. Such techniques include, but are not limited to: (1) hybridization of genomic DNA or cDNA libraries with probes to detect homologous nucleotide sequences; (2) antibody screening to detect polypeptides having shared structural features, for example, using an expression library; (3) polymerase chain reaction (PCR) on genomic DNA or cDNA using primers capable of annealing to a nucleic acid sequence of interest; (4) computer searches of sequence databases for related sequences; and (5) differential screening of a subtracted nucleic acid library.

Polynucleotides and polypeptides including modified forms can also be produced by chemical synthesis using methods known in the art, for example, an automated synthesis apparatus (see, e.g., Applied Biosystems, Foster City, Calif.). Peptides can be synthesized, whole or in part, using chemical methods (see. e.g., Caruthers (1980). Nucleic Acids Res. Symp. Ser. 215; Horn (1980); and Banga. A. K., Therapeutic Peptides and Proteins, Formulation, Processing and Delivery Systems (1995) Technomic Publishing Co., Lancaster, Pa.). Peptide synthesis can be performed using various solid phase techniques (see, e.g., Roberge Science 269:202 (1995); Merrifield, Methods Enzymol. 289:3(1997)) and automated synthesis may be achieved, e.g., using the ABI 431 A Peptide Synthesizer (Perkin Elmer) in accordance with the manufacturer's instructions.

Aspects may be better understood with reference to the following examples. These examples are intended to be representative of specific embodiments, but are not intended as limiting the overall scope of embodiments herein. Note that sequences herein including myc tags were included in the vector to aid in visualizing the distribution of the vector in the mice. The myc tag adds to the transgene length. In many embodiments it would not be used in clinical applications.

EXAMPLES

Figure 2:
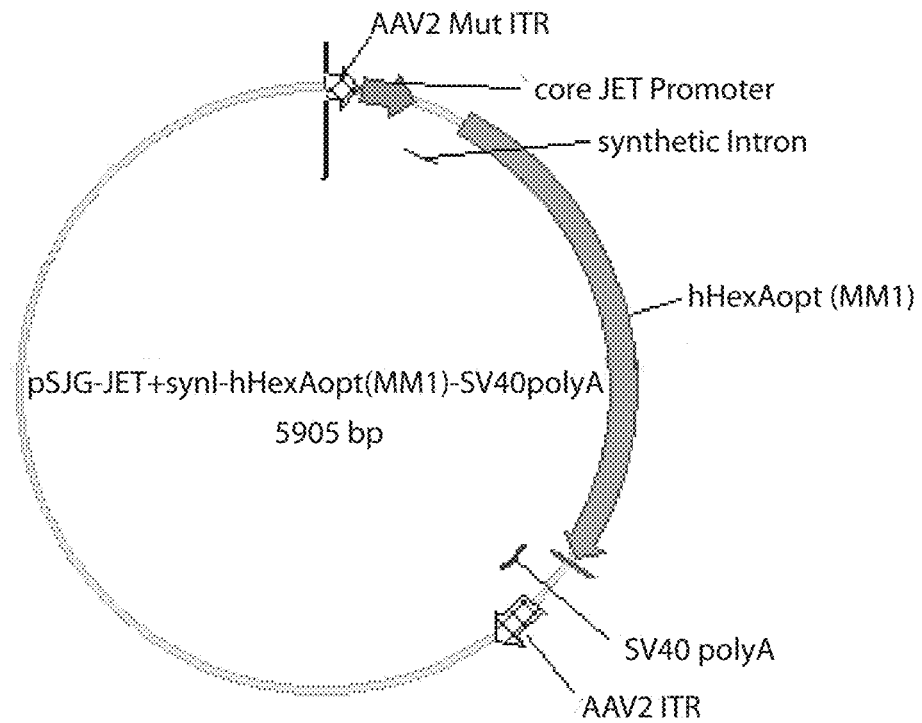
FIG. 2 is a diagram of an exemplary vector plasmid in accordance with various embodiments herein.

Example 1: Expression of Transgenes in CNS Tissue Using AAV Vector, JeT Promoter, and Synthetic Intron A self-complementary (sc) AAV genome was designed with a JeT promoter and synthetic intron sequence (SEQ ID NO: 4) to allow packaging of an optimized hexosaminidase HEXA (SEQ ID NO: 5 and FIG. 1 illustrate a plasmid sequence that includes portions of what was included within the AAV genome). A similar scAAV genome was designed with the same JeT promoter and intron sequence to allow packaging of a hexosaminidase variant known as HEXM (SEQ ID NO: 6 and FIG. 2 illustrate a plasmid sequence that includes portions of what was included within the AAV genome). Finally, a scAAV genome was designed with the same JeT promoter and intron sequence to allow packaging of a reporter gene (GFP green fluorescent protein) (SEQ ID NO: 7). These scAAV genomes were packaged into scAAV9 (serotype 9) vectors and injected stereotaxically into 4 or 15 month old TSD mice (e.g., either scAAV with HEXA or scAAV with HEXM was injected) along with an identical titer of the scAAV9/GFP vector to track vector spread.

The mice were euthanized after 4 weeks and brain sections were subjected to IHC analysis against GFP and GM2. The effectiveness of the JeT promoter plus intron sequence in causing expression of the third transgene (GFP) was assessed by the observed tissue fluorescence. The effectiveness of the JeT promoter plus intron sequence for the first and second scAAV vectors in causing expression of either the first (HEXA) or second (HEXM) transgenes was assessed by clearance of GM2 within the injected region, compared to the contralateral brain hemisphere. Qualitatively, a marked reduction of GM2 was apparent in the areas of highest GFP expression. All three vectors were observed to be effective for expression of their respective transgenes.

Example 2: Expression of a Hexosaminidase Protein in Sandhoff Mice Using AAV Vector, JeT Promoter, and Synthetic Intron Neonatal Sandhoff (beta deficient) mice were intravenously injected with a self-complementary vector (scAAV genome designed with a JeT promoter and a synthetic intron sequence (SEQ ID NO: 4) to allow packaging of a hexosaminidase variant known as HEXM—SEQ ID NO: 6 and FIG. 2 illustrate a plasmid sequence that includes portions of what was included within the AAV genome) for the expression of HexM at day 0-1. One cohort was monitored for 8 weeks and another cohort was monitored long-term (>40 weeks) for biochemical, behavioral and molecular analyses. Through the enzymatic and GM2 ganglioside lipid analyses, it was observed that with a slight increase in enzyme activity, there is a significant increase in the clearance of GM2 gangliosides. On behavioral tests, the treated mice outperform their knockout age matched controls. While the untreated controls die before the age of 15 weeks, treated animals have survived to more than 40 weeks. The molecular analyses reveal a uniform distribution of the vector between brain and spinal cord regions. The neonatal delivery of this newly synthesized viral vector expressing HexM to the Sandhoff mice provided long-term correction of the disease. This example shows the effectiveness of the JeT promoter plus intron sequence in expressing the hexosaminidase transgene as assessed by the increased enzyme activity and animal survival.

Example 3: UbC and JeT Promoter Evaluation

The objective of this example was to characterize the expression of the hrGFP reporter gene from constructs containing one of two promoters (UbC or JeT) and one of two intron lengths (140 bp—SEQ ID NO: 4 or 817 bp).

Naturally occurring adeno-associated virus (AAV) contains a single stranded DNA genome. Once the virus infects a cell complementary strands from different viruses must anneal or a complementary strand must be synthesized to create a stable molecule that can serve as a substrate for transcription. The need to anneal to a complementary strand or synthesize such strand reduces the overall transduction efficiency. To overcome this, a double stranded, self-complementary (scAAV) vector can be generated. scAAV does not require second strand synthesis and allows for lower concentrations of scAAV to be used, thus increasing transduction efficiency. However, because of the self-complementary nature of the viral genome the size of the expression cassette is more limited. Towards the goal of generating a scAAV production plasmid capable of expressing the HexA gene, the level of gene expression from the JeT and UbC promoters was characterized and how the length of an intron affects the level of expression was evaluated.

Figure 3:
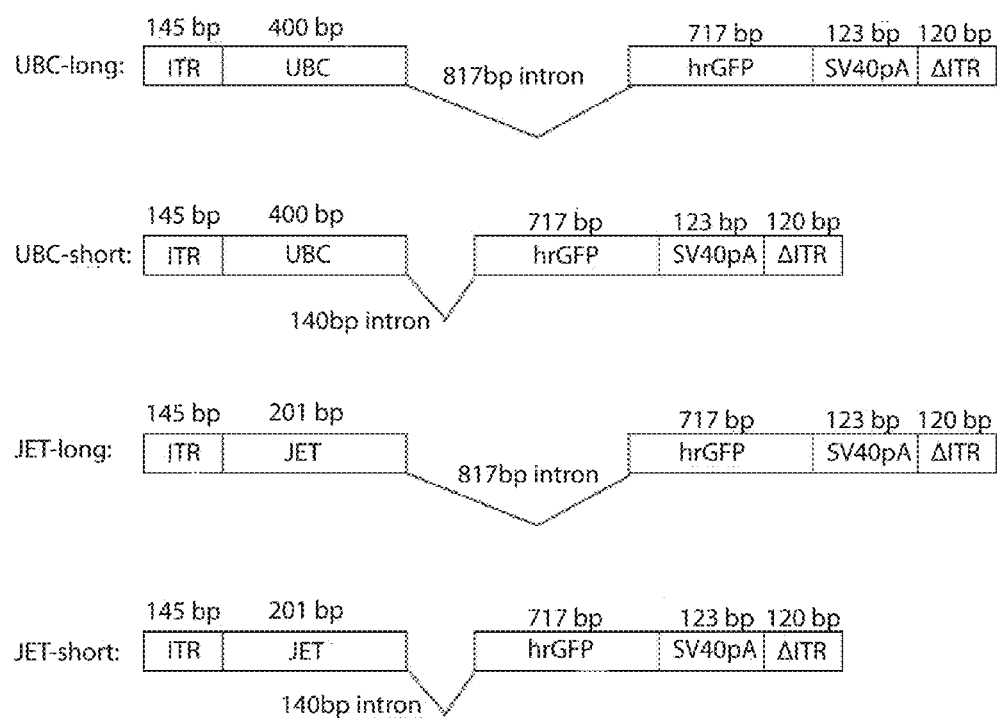
FIG. 3 is shows schematics of vectors used for example 3 herein.

Four mammalian expression plasmids were designed and constructed for these experiments. Standard molecular biology and PCR techniques were used to construct these expression vectors. These expression cassettes were cloned into the backbone of the pBLUESCRIPT plasmid (Stratagene). In general, PCR was used to modify the ends of the DNA fragments allowing for subcloning into subsequent vectors. The UBC promoter, long intron and SV40 polyadenylation sequence were recovered from pUB6/V5-His A (Invitrogen, cat. no. V250-01). Intron sequence (SEQ ID NO: 4) was used for the short synthetic intron. The sequence of the JeT promoter (SEQ ID NO: 2) was obtained from published literature (Gene 297 (2002) 21-32). The JeT promoter was generated using a PCR-based synthetic gene production strategy (modified from Gene, 164 (1995) 49-53). Using this approach, the ends of the JeT promoter were modified using PCR methods to allow for subsequent cloning events. The hrGFP gene was recovered from pAAV-hrGFP (Stratagene). Schematics of these vectors are shown in FIG. 3 (note that the length of the JeT promoter was listed as 201 bp because sequences joining the JeT promoter to the ITR were included in the count).

Figure 4:
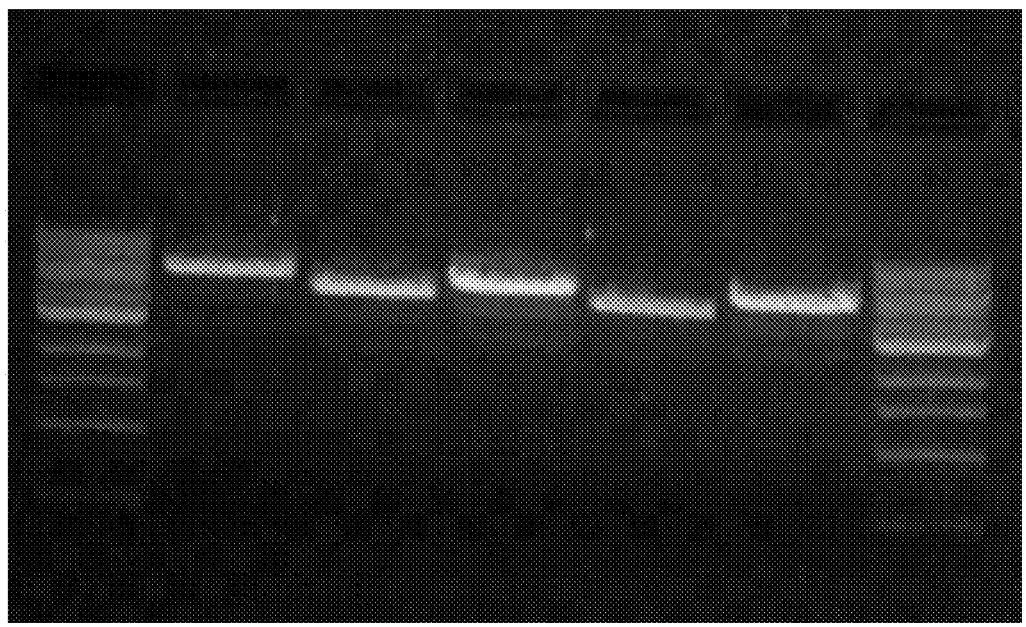
FIG. 4 is a picture of an agarose gel after electrophoresis of plasmid DNA after restriction endonuclease digestion as described in example 3 herein.

Large scale plasmid DNA isolations were completed for each of these plasmids along with the pAAV-hrGFP plasmid (CMV driven hrGFP). The plasmid DNA was quantified and the integrity assessed by restriction endonuclease digestion followed by agarose gel electrophoresis. The results of this characterization are shown in FIG. 4. All plasmid were of the correct size and at similar concentrations.

Figure 5:
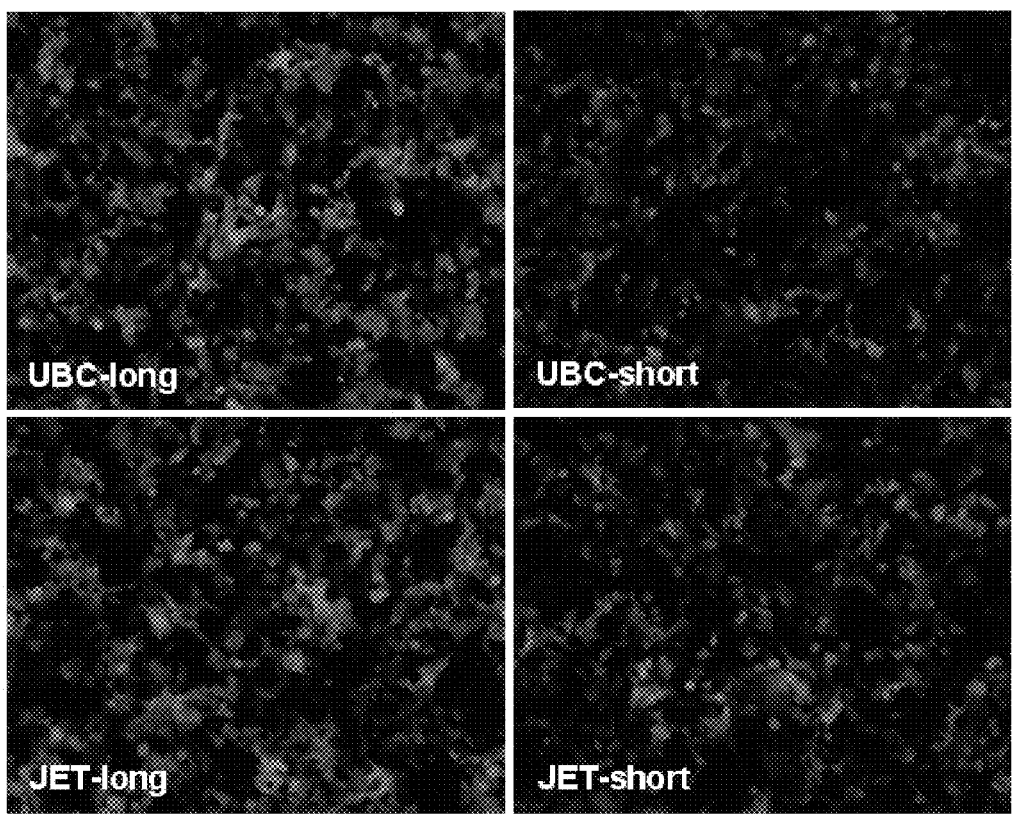
FIG. 5 shows images taken using fluorescence microscopy of hrGFP protein expression.

These plasmids were transfected into HEK293T cells in triplicate using Transit-293 transfection reagent (Mirus, Madison, Wis.) using the manufacturers recommended protocol. To normalize for the amount of transfected DNA, and to control for the difference in size of the plasmids, 1.89e11 DNA molecules were transfected into each of the wells. Forty-eight hours after transfection the amount of hrGFP protein expression was assessed using fluorescence microscopy (images shown in FIG. 5). From the images it appears that the longer intron leads to increased levels of protein expression. However, even the shorter intron is able to confer ample levels of hrGFP protein expression.

Figure 6:
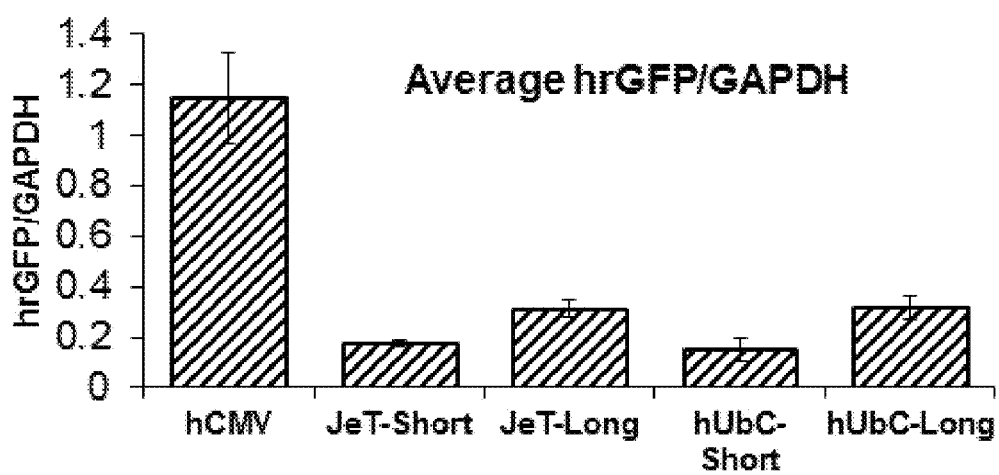
FIG. 6 is a graph showing hrGFP expression as normalized to GAPDH expression in a real-time PCR assay for different promoters.

Quantitative real-time PCR was used to determine the level of transcription from each of these constructs. Briefly, total RNA was isolated from the transfected cells using the mirVana miRNA isolation kit (Applied Biosystems, Foster City, Calif.) following the manufacturers recommended protocol. The transfected cells were homogenized in lysis/binding buffer using an Omni-Tip homogenization probe (Omni International, Kennesaw, Ga.). The total RNA was treated with DNase using the Turbo-DNA-free kit (Applied Biosystems, Foster City, Calif.). Random-primed cDNA was prepared from 500 ng of total RNA using the High Capacity cDNA synthesis kit from Applied Biosystems (Foster City, Calif.). The level of GAPDH and hrGFP expression was quantified using real-time PCR. hrGFP expression was normalized to GAPDH expression in each of the wells. The level of expression from each construct was determined by averaging the three independent wells. The results of this expression study are shown in FIG. 6.

It was found that both promoters drive expression of hrGFP to similar levels. Using the longer intron increases the level of hrGFP expression by about two fold. The use of the short intron still allows significant levels of hrGFP expression, albeit about one-fifth that of the CMV-hrGFP construct. Overall, the level of expression from these constructs is about 3-5 times lower than that observed from using the CMVhrGFP construct.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

Aspects have been described with reference to various specific and preferred embodiments and techniques. However, it should be understood that many variations and modifications may be made while remaining within the spirit and scope herein.

The invention claimed is:

1. A polynucleotide, comprising:
a JeT promoter or variant thereof,
a synthetic intron sequence less than 400 bases in length, the intron sequence having at least 90% sequence identity to SEQ ID NO: 11; and
a polynucleotide sequence encoding a polypeptide or protein, the sequence operatively linked to the promoter.

2. The polynucleotide of claim 1, wherein the JeT promoter or variant thereof has at least 90% sequence identity to a sequence selected from the group consisting of SEQ ID NO: 1, SEQ ID NO: 2, SEQ ID NO: 8, or SEQ ID NO: 10.

3. The polynucleotide of claim 1, wherein the JeT promoter or variant thereof has at least 90% sequence identity to at least one of SEQ ID NO: 14, SEQ ID NO: 15, and SEQ ID NO: 16 in the JeT promoter sequence from −36 to +42 relative to the transcription start site (Inr).

4. The polynucleotide of claim 1, wherein the JeT promoter or variant thereof has at least 99% sequence identity to at least one of SEQ ID NO: 14, SEQ ID NO: 15, and SEQ ID NO: 16 in the JeT promoter sequence from −36 to +42 relative to the transcription start site (Inr).

5. The polynucleotide of claim 1, wherein the JeT promoter or variant thereof has the nucleotides CT at locations +16 and +17 from the Inr A+1 transcription initiation site.

6. The polynucleotide of claim 1, the polypeptide or protein comprising a β-hexosaminidase protein, a subunit thereof, or a variant thereof.

7. The polynucleotide of claim 1, wherein the polynucleotide sequence encoding a polypeptide or protein is less than about 4.0 kilobases in length.

8. The polynucleotide of claim 1, wherein the polynucleotide sequence encoding a polypeptide or protein is between 1.2 and 2.0 kilobases in length.

9. The polynucleotide of claim 1, wherein the polynucleotide sequence encodes a polypeptide having at least 80% sequence identity to residues 89-529 of the alpha-subunit of Hex A (SEQ ID NO: 9) or conservative variants thereof.

10. A transgene expression system comprising
(a) a polynucleotide sequence comprising a transgene operably linked to a JeT promoter, or variant thereof, and a synthetic intron sequence of less than 400 bases in length, the intron sequence having at least 90% sequence identity to SEQ ID NO: 11; and
(b) a viral vector carrying the polynucleotide sequence.

11. The transgene expression system of claim 10, the viral vector comprising an adeno-associated virus (AAV) vector.

12. The transgene expression system of claim 10, wherein the JeT promoter or variant thereof has at least 90% sequence identity to a sequence selected from the group consisting of SEQ ID NO: 1, SEQ ID NO: 2, SEQ ID NO: 8, or SEQ ID NO: 10.

13. The transgene expression system of claim 10, the transgene coding for a β-hexosaminidase protein, a subunit thereof, or a variant thereof.

14. The transgene expression system of claim 10, the transgene encoding a polypeptide having at least 80% sequence identity to residues 89-529 of the alpha-subunit of Hex A (SEQ ID NO: 9) or conservative variants thereof.

15. The polynucleotide of claim 1, the intron sequence having at least 98% sequence identity to SEQ ID NO: 11.

16. The polynucleotide of claim 1, the intron sequence comprising SEQ ID NO: 11.

17. A polynucleotide, comprising:
a JeT promoter or variant thereof, wherein the JeT promoter or variant thereof has at least 90% sequence identity to a sequence selected from the group consisting of SEQ ID NO: 1, SEQ ID NO: 2, SEQ ID NO: 8, or SEQ ID NO: 10,
a synthetic intron sequence less than 400 bases in length, and
a polynucleotide sequence encoding a polypeptide or protein, the sequence operatively linked to the promoter.

18. The polynucleotide of claim 17, the polypeptide or protein comprising a β-hexosaminidase protein, a subunit thereof, or a variant thereof.

19. A transgene expression system comprising:
(a) a polynucleotide sequence comprising a transgene operably linked to a JeT promoter, or variant thereof, wherein the JeT promoter or variant thereof has at least 90% sequence identity to a sequence selected from the group consisting of SEQ ID NO: 1, SEQ ID NO: 2, SEQ ID NO: 8, or SEQ ID NO: 10, and a synthetic intron sequence of less than 400 bases in length; and
(b) a viral vector carrying the polynucleotide sequence.

20. The transgene expression system of claim 19, the viral vector comprising an adeno-associated virus (AAV) vector.

* * * * *

SEQUENCE LISTING

<160> NUMBER OF SEQ ID NOS: 18

<210> SEQ ID NO 1
<211> LENGTH: 195
<212> TYPE: DNA
<213> ORGANISM: Artificial Sequence
<220> FEATURE:
<223> OTHER INFORMATION: JeT Promoter
<220> FEATURE:
<221> NAME/KEY: promoter
<222> LOCATION: (1)..(195)

<400> SEQUENCE: 1

```
gaattcgggc ggagttaggg cggagccaat cagcgtgcgc cgttccgaaa gttgcctttt      60
atggctgggc ggagaatggg cggtgaacgc cgatgattat ataaggacgc gccgggtgtg     120
gcacagctag ttccgtcgca gccgggattt gggtcgcggt tcttgtttgt ggatccctgt     180
gatcgtcact tgaca                                                      195
```

<210> SEQ ID NO 2
<211> LENGTH: 192
<212> TYPE: DNA
<213> ORGANISM: Artificial Sequence
<220> FEATURE:
<223> OTHER INFORMATION: JeT Promoter
<220> FEATURE:
<221> NAME/KEY: promoter
<222> LOCATION: (1)..(192)

<400> SEQUENCE: 2

```
gaattcgggc ggagttaggg cggagccaat cagcgtgcgc cgttccgaaa gttgcctttt      60
atggctgggc ggagaatggg cggtgaacgc cgatgattat ataaggacgc gccgggtgtg     120
gcacagctag ttccgtcgca gccgggattt gggtcgcggt tcttgtttgt ggatccctgt     180
gatcgtcact tg                                                         192
```

<210> SEQ ID NO 3
<211> LENGTH: 10
<212> TYPE: DNA
<213> ORGANISM: Artificial Sequence
<220> FEATURE:
<223> OTHER INFORMATION: CArG element
<220> FEATURE:
<221> NAME/KEY: misc_feature
<222> LOCATION: (1)..(10)
<223> OTHER INFORMATION: CArG element

<400> SEQUENCE: 3

```
ccttttatgg                                                             10
```

<210> SEQ ID NO 4
<211> LENGTH: 140
<212> TYPE: DNA
<213> ORGANISM: Artificial Sequence
<220> FEATURE:
<223> OTHER INFORMATION: Synthetic Intron
<220> FEATURE:
<221> NAME/KEY: Intron
<222> LOCATION: (1)..(140)

<400> SEQUENCE: 4

```
gtaagtcact gactgtctat gcctgggaaa gggtgggcag gagatggggc agtgcaggaa      60
aagtggcact atgaaccctg cagccctagg aatgcatcta gacaattgta ctaaccttct     120
tctctttcct ctcctgacag                                                 140
```

<210> SEQ ID NO 5
<211> LENGTH: 5959
<212> TYPE: DNA
<213> ORGANISM: Artificial Sequence
<220> FEATURE:
<223> OTHER INFORMATION: Optimized Hexosaminidase HEXA
<220> FEATURE:
<221> NAME/KEY: misc_feature
<222> LOCATION: (1)..(5959)
<223> OTHER INFORMATION: Synthetic optimized hexosaminidase HEXA

<400> SEQUENCE: 5

| | | | | | |
|---|---|---|---|---|---|
| ctgcgcgctc | gctcgctcac | tgaggccgcc | cgggcaaagc | ccgggcgtcg | ggcgaccttt | 60 |
| ggtcgcccgg | cctcagtgag | cgagcgagcg | cgcagagagg | gagtgggggtt | cggtaccggg | 120 |
| cggagttagg | gcggagccaa | tcagcgtgcg | ccgttccgaa | agttgccttt | tatgctgggg | 180 |
| cggagaatgg | gcggtgaacg | ccgatgatta | tataaggacg | cgccgggtgt | ggcacagcta | 240 |
| gttccgtcgc | agccgggatt | tgggtcgcgg | ttcttgtttg | tggatccctg | tgatcgtcac | 300 |
| ttggtaagtc | actgactgtc | tatgcctggg | aaagggtggg | caggagatgg | ggcagtgcag | 360 |
| gaaaagtggc | actatgaacc | ctgcagccct | aggaatgcat | ctagacaatt | gtactaacct | 420 |
| tcttctcttt | cctctcctga | cagtccggaa | agccaccatg | acgtcctcca | gactgtggtt | 480 |
| ctcgctcttg | ttggcggcag | cgtttgccgg | aagggcaacc | gcgctctggc | cttggcccca | 540 |
| gaactttcag | acgtcagacc | agcgctatgt | gttgtaccct | aacaactttc | agtttcagta | 600 |
| tgacgtgtcg | tcagccgcgc | agccggggtg | ttcggtcctt | gatgaagcgt | tccaacgata | 660 |
| tcgagatctt | ctgtttgggt | cggggtcctg | gcctagaccc | tacctcaccg | ggaagcgcca | 720 |
| cacgcttgaa | aagaatgtac | ttgtcgtgag | cgtggtaaca | cccggatgca | atcagcttcc | 780 |
| cactcttgaa | agcgtggaaa | actacacgtt | gacgatcaac | gatgatcagt | gcttgctcct | 840 |
| gtcagagaca | gtgtggggtg | cgctgagggg | actcgaaact | ttctcacagc | ttgtctggaa | 900 |
| gtccgcagag | ggcacgttct | tcatcaacaa | aacggaaatc | gaggatttcc | cccgatttcc | 960 |
| tcatcgcggg | cttcttctgg | ataccagccg | gcactacctc | ccactgtcat | cgattctgga | 1020 |
| cacacttgac | gtaatggctt | acaacaaact | caatgtgttt | cactggcatt | tggtggatga | 1080 |
| cccgtccttt | ccttacgaat | ccttcacttt | ccccgagctg | atgagaaaag | gaagctataa | 1140 |
| tccggtgacc | cacatctaca | cagcgcaaga | cgtcaaggag | gtaatcgagt | atgcgaggtt | 1200 |
| gcggggcatt | cgcgtgctgg | cagagtttga | cacccccggt | catacgctgt | cgtggggggcc | 1260 |
| agggattccc | ggtttgttga | cgccttgtta | ttcggggtca | gagccgagcg | gaacgttcgg | 1320 |
| acctgtcaat | ccgtccctga | ataacactta | cgagtttatg | agcactttct | tcttggaggt | 1380 |
| gtcgtccgta | ttcccagact | tctaccttca | tctgggcggt | gatgaagtgg | actttacttg | 1440 |
| ctggaaaagc | aacccggaga | tccaagattt | catgcgcaaa | aagggattcg | gagaggactt | 1500 |
| taaacaactt | gagtcattct | atattcaaac | actccttgat | atcgtatcgt | cgtacggaaa | 1560 |
| agggtatgtc | gtctggcagg | aagtgttcga | caacaaagtc | aagattcagc | ccgatacgat | 1620 |
| cattcaagtg | tggagggagg | acatccccgt | gaactatatg | aaggagctcg | aactcgtcac | 1680 |
| aaaggctgga | ttcagagcgt | tgcttttcagc | gccttggtac | ttgaatcgca | tttcgtatgg | 1740 |
| tccccgattgg | aaggactttt | acatcgtgga | gccccctcgca | ttcgaaggga | ccccggagca | 1800 |
| gaaggcgttg | gtgattgggg | gtgaggcgtg | catgtgggga | gagtacgtcg | acaatactaa | 1860 |
| tcttgtcccg | cgcttgtggc | cgagggctgg | agccgtcgcc | gaaaggctct | ggagcaataa | 1920 |
| gttgacgtcg | gacctgacgt | tcgcctacga | gcggctctcc | cactttcggt | gcgaactcct | 1980 |

```
ccggcgagga gtacaggcac aaccccttaa cgtaggtttt tgtgagcagg aatttgaaca    2040
gacatctaga gggcccttcg aacaaaaact catctcagaa gaggatctgg tcgactgata    2100
actcgagtgt ttattgcagc ttataatggt tacaaataaa gcaatagcat cacaaatttc    2160
acaaataaag catttttttc actgcattct agttgtggtt tgtccaaact catcaatgta    2220
tcttatcatg acgcgtagga acccctagtg atggagttgg ccactccctc tctgcgcgct    2280
cgctcgctca ctgaggccgg gcgaccaaag gtcgcccgac gcccgggctt tgcccgggcg    2340
gcctcagtga gcgagcgagc gcgcagctgg cgtaatagcg aagaggcccg caccgatcgc    2400
ccttcccaac agttgcgcag cctgaatggc gaatggcgat tccgttgcaa tggctggcgg    2460
taatattgtt ctggatatta ccagcaaggc cgatagtttg agttcttcta ctcaggcaag    2520
tgatgttatt actaatcaaa gaagtattgc gacaacggtt aatttgcgtg atggacagac    2580
tcttttactc ggtggcctca ctgattataa aaacacttct caggattctg gcgtaccgtt    2640
cctgtctaaa atccctttaa tcggcctcct gtttagctcc cgctctgatt ctaacgagga    2700
aagcacgtta tacgtgctcg tcaaagcaac catagtacgc gccctgtagc ggcgcattaa    2760
gcgcggcggg tgtggtggtt acgcgcagcg tgaccgctac acttgccagc gccctagcgc    2820
ccgctccttt cgctttcttc ccttcctttc tcgccacgtt cgccggcttt ccccgtcaag    2880
ctctaaatcg ggggctccct ttagggttcc gatttagtgc tttacggcac ctcgacccca    2940
aaaaacttga ttagggtgat ggttcacgta gtgggccatc gccctgatag acggtttttc    3000
gccctttgac gttggagtcc acgttcttta atagtggact cttgttccaa actggaacaa    3060
cactcaaccc tatctcggtc tattcttttg atttataagg gattttgccg atttcggcct    3120
attggttaaa aaatgagctg atttaacaaa aatttaacgc gaattttaac aaaatattaa    3180
cgtttacaat ttaaatattt gcttatacaa tcttcctgtt tttggggctt ttctgattat    3240 caaccgggt acatatgatt gacatgctag ttttacgatt accgttcatc gattctcttg    3300
tttgctccag actctcaggc aatgacctga tagcctttgt agagacctct caaaaatagc    3360
taccctctcc ggcatgaatt tatcagctag aacggttgaa tatcatattg atggtgattt    3420
gactgtctcc ggcctttctc acccgtttga atctttacct acacattact caggcattgc    3480
atttaaaata tatgagggtt ctaaaaattt ttatccttgc gttgaaataa aggcttctcc    3540
cgcaaaagta ttacagggtc ataatgtttt tggtacaacc gatttagctt tatgctctga    3600
ggctttattg cttaattttg ctaattcttt gccttgcctg tatgatttat tggatgttgg    3660
aattcctgat gcggtatttt ctccttacgc atctgtgcgg tatttcacac cgcatatggt    3720
gcactctcag tacaatctgc tctgatgccg catagttaag ccagccccga cacccgccaa    3780
cacccgctga cgcgccctga cgggcttgtc tgctcccggc atccgcttac agacaagctg    3840
tgaccgtctc cggagctgc atgtgtcaga ggttttcacc gtcatcaccg aaacgcgcga    3900
gacgaaaggg cctcgtgata cgcctatttt tataggttaa tgtcatgata ataatggttt    3960
cttagacgtc aggtggcact tttcggggaa atgtgcgcgg aacccctatt tgtttatttt    4020
tctaaataca ttcaaatatg tatccgctca tgagacaata accctgataa atgcttcaat    4080
aatattgaaa aaggaagagt atgagtattc aacatttccg tgtcgccctt attccctttt    4140
ttgcggcatt ttgccttcct gttttgctc acccagaaac gctggtgaaa gtaaaagatg    4200
ctgaagatca gttgggtgca cgagtgggtt acatcgaact ggatctcaac agcggtaaga    4260
tccttgagag ttttcgcccc gaagaacgtt ttccaatgat gagcactttt aaagttctgc    4320
```

| | |
|---|---|
| tatgtggcgc ggtattatcc cgtattgacg ccgggcaaga gcaactcggt cgccgcatac | 4380 |
| actattctca gaatgacttg gttgagtact caccagtcac agaaaagcat cttacggatg | 4440 |
| gcatgacagt aagagaatta tgcagtgctg ccataaccat gagtgataac actgcggcca | 4500 |
| acttacttct gacaacgatc ggaggaccga aggagctaac cgcttttttg cacaacatgg | 4560 |
| gggatcatgt aactcgcctt gatcgttggg aaccggagct gaatgaagcc ataccaaacg | 4620 |
| acgagcgtga caccacgatg cctgtagcaa tggcaacaac gttgcgcaaa ctattaactg | 4680 |
| gcgaactact tactctagct tcccggcaac aattaataga ctggatggag gcggataaag | 4740 |
| ttgcaggacc acttctgcgc tcggcccttc cggctggctg gtttattgct gataaatctg | 4800 |
| gagccggtga gcgtgggtct cgcggtatca ttgcagcact ggggccagat ggtaagccct | 4860 |
| cccgtatcgt agttatctac acgacgggga gtcaggcaac tatggatgaa cgaaatagac | 4920 |
| agatcgctga gataggtgcc tcactgatta agcattggta actgtcagac caagtttact | 4980 |
| catatatact ttagattgat ttaaaacttc attttttaatt taaaaggatc taggtgaaga | 5040 |
| tcctttttga taatctcatg accaaaatcc cttaacgtga gttttcgttc cactgagcgt | 5100 |
| cagaccccgt agaaaagatc aaaggatctt cttgagatcc ttttttttctg cgcgtaatct | 5160 |
| gctgcttgca acaaaaaaa ccaccgctac cagcggtggt ttgtttgccg gatcaagagc | 5220 |
| taccaactct ttttccgaag gtaactggct tcagcagagc gcagatacca aatactgtcc | 5280 |
| ttctagtgta gccgtagtta ggccaccact tcaagaactc tgtagcaccg cctacatacc | 5340 |
| tcgctctgct aatcctgtta ccagtggctg ctgccagtgg cgataagtcg tgtcttaccg | 5400 |
| ggttggactc aagacgatag ttaccggata aggcgcagcg tcgggctga acggggggtt | 5460 |
| cgtgcacaca gcccagcttg gagcgaacga cctacaccga actgagatac ctacagcgtg | 5520 |
| agctatgaga aagcgccacg cttcccgaag ggagaaaggc ggacaggtat ccggtaagcg | 5580 |
| gcagggtcgg aacaggagag cgcacgaggg agcttccagg gggaaacgcc tggtatcttt | 5640 |
| atagtcctgt cgggtttcgc cacctctgac ttgagcgtcg attttttgtga tgctcgtcag | 5700 |
| gggggcggag cctatggaaa aacgccagca acgcggcctt tttacggttc ctggccttttt | 5760 |
| gctggccttt tgctcacatg ttctttcctg cgttatcccc tgattctgtg ataaccgta | 5820 |
| ttaccgcctt tgagtgagct gataccgctc gccgcagccg aacgaccgag cgcagcgagt | 5880 |
| cagtgagcga ggaagcggaa gagcgcccaa tacgcaaacc gcctctcccc gcgcgttggc | 5940 |
| cgattcatta atgcagcag | 5959 |

<210> SEQ ID NO 6
<211> LENGTH: 5905
<212> TYPE: DNA
<213> ORGANISM: Artificial Sequence
<220> FEATURE:
<223> OTHER INFORMATION: Hexosaminidase variant known as HEXM
<220> FEATURE:
<221> NAME/KEY: misc_feature
<222> LOCATION: (1)..(5905)
<223> OTHER INFORMATION: Variant of hexosaminidase known as HEXM

<400> SEQUENCE: 6

| | |
|---|---|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtggggtt cggtaccggg | 120 |
| cggagttagg gcggagccaa tcagcgtgcg ccgttccgaa agttgccttt tatggctggg | 180 |
| cggagaatgg gcggtgaacg ccgatgatta tataaggacg cgccgggtgt ggcacagcta | 240 |
| gttccgtcgc agccgggatt tgggtcgcgg ttcttgtttg tggatccctg tgatcgtcac | 300 |

```
ttggtaagtc actgactgtc tatgcctggg aaagggtggg caggagatgg ggcagtgcag    360
gaaaagtggc actatgaacc ctgcagccct aggaatgcat ctagacaatt gtactaacct    420
tcttctcttt cctctcctga cagtccggaa agccaccatg acctcttcta gactgtggtt    480
cagcctgctg ctcgccgcag cctttgccgg acgggccacc gctctttggc cgtggcccca    540
gaacttccag acctctgacc agcggtacgt gctttaccca ataacttcc agtttcagta     600 cgatgtgtcc agcgccgctc agccgggctg ttccgtgctg gacgaggcct ccaacgcta     660 tcgcgacctt cttttcggat ctggctcctg gccaaggcca tatctcaccg gaaagagaca    720 caccettgag aagaacgtcc tcgtggtgag cgtggtgacc cctggttgta atcaactgcc    780
gaccctggaa tctgtcgaga attacactct gactattaac gacgaccaat gcctgcttct    840
gtctgaaact gtctggggag cactgcgggg acttgaaacc ttcagccagc tggtgtggaa    900
gtcagcagag ggaaccttct tcatcaataa gaccgaaatc gaggattttc cccgcttccc    960
tcatcgggga ctgctgctgg acactagccg ccattatctt ccgcttaagt ccattctgga   1020
taccctcgac gtgatggcat acaacaaact caatgtgttc cactggcatc tggtggacga   1080
ccagtcattt ccctacgagt ccttcacctt ccccgaactc atgaggaagg gaagctactc   1140
tctcagccac atctacaccg cccaagacgt caaggaagtc atcgaatatg cacgcctgcg   1200
cggaattaga gtgctcgccg agttcgacac ccctgggcac accctgagct ggggacctgg   1260
catccctggt ctgctcactc cctgctattc agggtcagaa ccttccggta cttttggccc   1320
tgtcaatcct agcctgaaca atacttacga gtttatgtct actttcttcc ttgaagtctc   1380
atcagtcttt ccagacttct atctgcatct cggaggtgat gaagtggact tcacctgttg   1440
gaagtcaaac cccgaaattc aagactttat gcggaagaag ggtttcggag aggatttcaa   1500
acaactggag agcttctaca tccagaccct tctcgacatc gtgtcctcat acgggaaagg   1560
ttacgtggtc tggcaggaag tgttcgacaa taaggtgaag attcagcccg acaccattat   1620
ccaagtctgg cgggaggaca tcccagtgaa ctacatgaag gaacttgagc tggtgactaa   1680
ggctgggttc cgcgctcttc tcagcgctcc atggtatctc aatcggatct cttacggaca   1740
ggattggagg aagttctaca agtcgaacc cctggctttc gaggggaccc ctgagcagaa    1800
ggctcttgtg atcggaggcg aggcctgcat gtggggagag tacgtggatg ccaccaacct   1860
ggtgcccaga ctttggccaa gggccggtgc cgtggctgaa cgcctgtggt caaataagct   1920
gacccgcgat atggacgacg cctatgatag actttcacat ttccggtgcg aactggtgcg   1980
gagaggggtg gctgcccagc cgctgtacgc cgggtactgc aaccaggagt ttgagcagac   2040
ttaatagctc gagtgtttat tgcagcttat aatggttaca ataaagcaa tagcatcaca    2100 aatttcacaa ataaagcatt tttttcactg cattctagtt gtggtttgtc caaactcatc   2160
aatgtatctt atcatgacgc gtaggaaccc ctagtgatgg agttggccac tccctctctg   2220
cgcgctcgct cgctcactga ggccgggcga ccaaaggtcg cccgacgccc gggctttgcc   2280
cgggcggcct cagtgagcga gcgagcgcgc agctggcgta atagcgaaga ggcccgcacc   2340
gatcgccctt cccaacagtt gcgcagcctg aatggcgaat ggcgattccg ttgcaatggc   2400
tggcggtaat attgttctgg atattaccag caaggccgat agtttgagtt cttctactca   2460
ggcaagtgat gttattacta atcaaagaag tattgcgaca acggttaatt tgcgtgatgg   2520
acagactctt ttactcggtg gcctcactga ttataaaaac acttctcagg attctggcgt   2580
accgttcctg tctaaaatcc ctttaatcgg cctcctgttt agctcccgct ctgattctaa   2640
```

```
cgaggaaagc acgttatacg tgctcgtcaa agcaaccata gtacgcgccc tgtagcggcg    2700
cattaagcgc ggcgggtgtg gtggttacgc gcagcgtgac cgctacactt gccagcgccc    2760
tagcgcccgc tcctttcgct ttcttccctt cctttctcgc cacgttcgcc ggctttcccc    2820
gtcaagctct aaatcggggg ctcccttta g gttccgatt tagtgcttta cggcacctcg    2880
accccaaaaa acttgattag ggtgatggtt cacgtagtgg gccatcgccc tgatagacgg    2940
tttttcgccc tttgacgttg gagtccacgt tctttaatag tggactcttg ttccaaactg    3000
gaacaacact caaccctatc tcggtctatt cttttgattt ataagggatt ttgccgattt    3060
cggcctattg gttaaaaaat gagctgattt aacaaaaatt taacgcgaat tttaacaaaa    3120
tattaacgtt tacaatttaa atatttgctt atacaatctt cctgtttttg ggcttttct     3180 gattatcaac cggggtacat atgattgaca tgctagtttt acgattaccg ttcatcgatt    3240
ctcttgtttg ctccagactc tcaggcaatg acctgatagc ctttgtagag acctctcaaa    3300
aatagctacc ctctccggca tgaatttatc agctagaacg gttgaatatc atattgatgg    3360
tgatttgact gtctccggcc tttctcaccc gtttgaatct ttacctacac attactcagg    3420
cattgcattt aaaatatatg agggttctaa aaattttat ccttgcgttg aaataaaggc     3480
ttctcccgca aaagtattac agggtcataa tgttttggt acaaccgatt tagctttatg     3540
ctctgaggct ttattgctta attttgctaa ttctttgcct tgcctgtatg atttattgga    3600
tgttggaatt cctgatgcgg tatttctcc ttacgcatct gtgcggtatt tcacaccgca     3660
tatggtgcac tctcagtaca atctgctctg atgccgcata gttaagccag ccccgacacc    3720
cgccaacacc cgctgacgcg ccctgacggg cttgtctgct cccggcatcc gcttacagac    3780
aagctgtgac cgtctccggg agctgcatgt gtcagaggtt ttcaccgtca tccgaaac     3840 gcgcgagacg aaagggcctc gtgatacgcc tatttttata ggttaatgtc atgataataa    3900
tggtttctta gacgtcaggt ggcacttttc ggggaaatgt gcgcggaacc cctatttgtt    3960
tatttttcta aatacattca aatatgtatc cgctcatgag acaataaccc tgataaatgc    4020
ttcaataata ttgaaaaagg aagagtatga gtattcaaca tttccgtgtc gcccttattc    4080
ccttttttgc ggcattttgc cttcctgttt ttgctcaccc agaaacgctg gtgaaagtaa    4140
aagatgctga agatcagttg ggtgcacgag tgggttacat cgaactggat ctcaacagcg    4200
gtaagatcct tgagagtttt cgccccgaag aacgttttcc aatgatgagc acttttaaag    4260
ttctgctatg tggcgcggta ttatcccgta ttgacgccgg gcaagagcaa ctcggtcgcc    4320
gcatacacta ttctcagaat gacttggttg agtactcacc agtcacagaa aagcatctta    4380
cggatggcat gacagtaaga gaattatgca gtgctgccat aaccatgagt gataacactg    4440
cggccaactt acttctgaca acgatcggag gaccgaagga gctaaccgct ttttgcaca    4500 acatggggga tcatgtaact cgccttgatc gttgggaacc ggagctgaat gaagccatac    4560
caaacgacga gcgtgacacc acgatgcctg tagcaatggc aacaacgttg cgcaaactat    4620
taactggcga actacttact ctagcttccc ggcaacaatt aatagactgg atggaggcgg    4680
ataaagttgc aggaccactt ctgcgctcgg cccttccggc tggctggttt attgctgata    4740
aatctggagc cggtgagcgt gggtctcgcg gtatcattgc agcactgggg ccagatggta    4800
agccctcccg tatcgtagtt atctacacga cggggagtca ggcaactatg gatgaacgaa    4860
atagacagat cgctgagata ggtgcctcac tgattaagca ttggtaactg tcagaccaag    4920
tttactcata tatactttag attgatttaa aacttcattt ttaatttaaa aggatctagg    4980
tgaagatcct tttgataat c tcatgacca aaatccctta acgtgagttt tcgttccact    5040
```

```
gagcgtcaga ccccgtagaa aagatcaaag gatcttcttg agatccttt  tttctgcgcg    5100 taatctgctg cttgcaaaca aaaaaaccac cgctaccagc ggtggtttgt ttgccggatc    5160
aagagctacc aactctttt  ccgaaggtaa ctggcttcag cagagcgcag ataccaaata    5220
ctgtccttct agtgtagccg tagttaggcc accacttcaa gaactctgta gcaccgccta    5280
catacctcgc tctgctaatc ctgttaccag tggctgctgc cagtggcgat aagtcgtgtc    5340
ttaccgggtt ggactcaaga cgatagttac cggataaggc gcagcggtcg ggctgaacgg    5400
ggggttcgtg cacacagccc agcttggagc gaacgaccta ccgaactg  agatacctac    5460 agcgtgagct atgagaaagc gccacgcttc ccgaagggag aaaggcggac aggtatccgg    5520
taagcggcag ggtcggaaca ggagagcgca cgagggagct tccaggggga acgcctggt     5580 atctttatag tcctgtcggg tttcgccacc tctgacttga gcgtcgattt ttgtgatgct    5640 cgtcagggg  gcggagccta tggaaaaacg ccagcaacgc ggccttttta cggttcctgg    5700
ccttttgctg gccttttgct cacatgttct ttcctgcgtt atcccctgat tctgtggata    5760
accgtattac cgcctttgag tgagctgata ccgctcgccg cagccgaacg accgagcgca    5820
gcgagtcagt gagcgaggaa gcggaagagc gcccaatacg caaaccgcct ctccccgcgc    5880
gttggccgat tcattaatgc agcag                                         5905
```

```
<210> SEQ ID NO 7
<211> LENGTH: 4135
<212> TYPE: DNA
<213> ORGANISM: Artificial Sequence
<220> FEATURE:
<223> OTHER INFORMATION: scAAV genome with JeT promoter, intron sequence
      and GFP reporter
<220> FEATURE:
<221> NAME/KEY: promoter
<222> LOCATION: (695)..(886)
<223> OTHER INFORMATION: JeT promoter
<220> FEATURE:
<221> NAME/KEY: Intron
<222> LOCATION: (887)..(1026)
<223> OTHER INFORMATION: synthetic intron
<220> FEATURE:
<221> NAME/KEY: gene
<222> LOCATION: (1058)..(1774)
<223> OTHER INFORMATION: green fluorescent protein reporter gene
<220> FEATURE:
<221> NAME/KEY: polyA_signal
<222> LOCATION: (1791)..(1918)
<223> OTHER INFORMATION: SV40 polyadenylation sequence

<400> SEQUENCE: 7
ctaaattgta agcgttaata ttttgttaaa attcgcgtta aattttttgtt aaatcagctc     60 attttttaac caataggccg aaatcggcaa atcccttat  aaatcaaaag aatagaccga    120
gatagggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt tttttggggt cgaggtgccg taaagcacta aatcggaacc ctaaagggag    300
cccccgattt agagcttgac ggggaaagcc ggcgaacgtg gcgagaaagg aagggaagaa    360
agcgaaagga gcggcgcta  gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggcgaat tggagctcca    660
```

```
ccgcggtggc ggccgctcta gcacgcgtgg atctgaattc gggcggagtt agggcggagc    720
caatcagcgt gcgccgttcc gaaagttgcc ttttatggct gggcggagaa tgggcggtga    780
acgccgatga ttatataagg acgcgccggg tgtggcacag ctagttccgt cgcagccggg    840
atttgggtcg cggttcttgt tgtggatcc ctgtgatcgt cacttggtaa gtcactgact     900
gtctatgcct gggaaagggt gggcaggaga tggggcagtg caggaaaagt ggcactatga    960
accctgcagc cctaggaatg catctagaca attgtactaa ccttcttctc tttcctctcc   1020
tgacagacga agcttgtcta tatcgattga attcaccatg gtgagcaagc agatcctgaa   1080
gaacaccggc ctgcaggaga tcatgagctt caaggtgaac ctggagggcg tggtgaacaa   1140
ccacgtgttc accatggagg gctgcggcaa gggcaacatc ctgttcggca ccagctggt    1200 gcagatccgc gtgaccaagg cgcccccct gcccttcgcc ttcgacatcc tgagccccgc    1260
cttccagtac ggcaaccgca ccttcaccaa gtaccccgag acatcagcg acttcttcat    1320 ccagagcttc cccgccggct tcgtgtacga gcgcaccctg cgctacgagg acggcggcct   1380
ggtggagatc cgcagcgaca tcaacctgat cgaggagatg ttcgtgtacc gcgtggagta   1440
caagggccga aacttccca cgacggccc cgtgatgaag aagaccatca ccggcctgca    1500
gcccagcttc gaggtggtgt acatgaacga cggcgtgctg gtgggccagg tgatcctggt   1560
gtaccgcctg aacagcggca agttctacag ctgccacatg cgcaccctga tgaagagcaa   1620
gggcgtggtg aaggacttcc ccgagtacca cttcatccag caccgcctgg agaagaccta   1680
cgtggaggac ggcggcttcg tggagcagca cgagaccgcc atcgcccagc tgaccagcct   1740
gggcaagccc ctgggcagcc tgcacgagtg ggtgtaatag ctcgagagat cttgtttatt   1800
gcagcttata atggttacaa ataaagcaat agcatcacaa atttcacaaa taaagcattt   1860
ttttcactgc attctagttg tggtttgtcc aaactcatca atgtatctta tcatggctag   1920
ccggaccgtg tacccagctt tgttcccctt tagtgagggt taattgcgcg cttggcgtaa   1980
tcatggtcat agctgtttcc tgtgtgaaat tgttatccgc tcacaattcc acacaacata   2040
cgagccggaa gcataaagtg taagcctggg gtgcctaat gagtgagcta actcacatta    2100
attgcgttgc gctcactgcc cgctttccag tcgggaaacc tgtcgtgcca gctgcattaa   2160
tgaatcggcc aacgcgcggg gagaggcggt ttgcgtattg ggcgctcttc cgcttcctcg   2220
ctcactgact cgctgcgctc ggtcgttcgg ctgcggcgag cggtatcagc tcactcaaag   2280
gcggtaatac ggttatccac agaatcaggg gataacgcag gaaagaacat gtgagcaaaa   2340
ggccagcaaa aggccaggaa ccgtaaaaag gccgcgttgc tggcgttttt ccataggctc   2400 cgccccctg acgagcatca caaaatcga cgctcaagtc agaggtggcg aaacccgaca    2460
ggactataaa gataccaggc gtttccccct ggaagctccc tcgtgcgctc tcctgttccg   2520
accctgccgc ttaccggata cctgtccgcc tttctccctt cgggaagcgt ggcgctttct   2580
catagctcac gctgtaggta tctcagttcg gtgtaggtcg ttcgctccaa gctgggctgt   2640
gtgcacgaac cccccgttca gcccgaccgc tgcgccttat ccggtaacta tcgtcttgag   2700
tccaacccgg taagacacga cttatcgcca ctggcagcag ccactggtaa caggattagc   2760
agagcgaggt atgtaggcgg tgctacagag ttcttgaagt ggtggcctaa ctacggctac   2820
actagaagga cagtatttgg tatctgcgct ctgctgaagc cagttacctt cggaaaaaga   2880
gttggtagct cttgatccgg caaacaaacc accgctggta gcggtggttt ttttgtttgc   2940
aagcagcaga ttacgcgcag aaaaaaagga tctcaagaag atcctttgat ctttctacg    3000
```

-continued

```
gggtctgacg ctcagtggaa cgaaaactca cgttaaggga ttttggtcat gagattatca    3060
aaaaggatct tcacctagat cctttaaat taaaatgaa gttttaaatc aatctaaagt      3120
atatatgagt aaacttggtc tgacagttac caatgcttaa tcagtgaggc acctatctca    3180
gcgatctgtc tatttcgttc atccatagtt gcctgactcc ccgtcgtgta gataactacg    3240
atacgggagg gcttaccatc tggccccagt gctgcaatga taccgcgaga cccacgctca    3300
ccggctccag atttatcagc aataaaccag ccagccggaa gggccgagcg cagaagtggt    3360
cctgcaactt tatccgcctc catccagtct attaattgtt gccgggaagc tagagtaagt    3420
agttcgccag ttaatagttt gcgcaacgtt gttgccattg ctacaggcat cgtggtgtca    3480
cgctcgtcgt ttggtatggc ttcattcagc tccggttccc aacgatcaag gcgagttaca    3540
tgatccccca tgttgtgcaa aaaagcggtt agctccttcg gtcctccgat cgttgtcaga    3600
agtaagttgg ccgcagtgtt atcactcatg gttatggcag cactgcataa ttctcttact    3660
gtcatgccat ccgtaagatg cttttctgtg actggtgagt actcaaccaa gtcattctga    3720
gaatagtgta tgcggcgacc gagttgctct tgcccggcgt caatacggga taataccgcg    3780
ccacatagca gaactttaaa agtgctcatc attggaaaac gttcttcggg gcgaaaactc    3840
tcaaggatct taccgctgtt gagatccagt tcgatgtaac ccactcgtgc acccaactga    3900
tcttcagcat cttttacttt caccagcgtt tctgggtgag caaaaacagg aaggcaaaat    3960
gccgcaaaaa agggaataag ggcgacacgg aaatgttgaa tactcatact cttccttttt    4020
caatattatt gaagcattta tcagggttat tgtctcatga gcggatacat atttgaatgt    4080
atttagaaaa ataaacaaat aggggttccg cgcacatttc cccgaaaagt gccac         4135
```

<210> SEQ ID NO 8
<211> LENGTH: 187
<212> TYPE: DNA
<213> ORGANISM: Artificial Sequence
<220> FEATURE:
<223> OTHER INFORMATION: JeT Promoter
<220> FEATURE:
<221> NAME/KEY: promoter
<222> LOCATION: (1)..(187)
<223> OTHER INFORMATION: JeT promoter

<400> SEQUENCE: 8

```
cgggcggagt tagggcggag ccaatcagcg tgcgccgttc cgaaagttgc cttttatggc     60
tgggcggaga atgggcggtg aacgccgatg attatataag gacgcgccgg gtgtggcaca    120
gctagttccg tcgcagccgg gatttgggtc gcggttcttg tttgtggatc cctgtgatcg    180
tcacttg                                                              187
```

<210> SEQ ID NO 9
<211> LENGTH: 529
<212> TYPE: PRT
<213> ORGANISM: Homo sapiens

<400> SEQUENCE: 9

```
Met Thr Ser Ser Arg Leu Trp Phe Ser Leu Leu Leu Ala Ala Ala Phe
1               5                   10                  15

Ala Gly Arg Ala Thr Ala Leu Trp Pro Trp Pro Gln Asn Phe Gln Thr
            20                  25                  30

Ser Asp Gln Arg Tyr Val Leu Tyr Pro Asn Asn Phe Gln Phe Gln Tyr
        35                  40                  45

Asp Val Ser Ser Ala Ala Gln Pro Gly Cys Ser Val Leu Asp Glu Ala
    50                  55                  60
```

```
Phe Gln Arg Tyr Arg Asp Leu Leu Phe Gly Ser Gly Ser Trp Pro Arg
 65                  70                  75                  80

Pro Tyr Leu Thr Gly Lys Arg His Thr Leu Glu Lys Asn Val Leu Val
                 85                  90                  95

Val Ser Val Val Thr Pro Gly Cys Asn Gln Leu Pro Thr Leu Glu Ser
            100                 105                 110

Val Glu Asn Tyr Thr Leu Thr Ile Asn Asp Asp Gln Cys Leu Leu Leu
            115                 120                 125

Ser Glu Thr Val Trp Gly Ala Leu Arg Gly Leu Glu Thr Phe Ser Gln
            130                 135                 140

Leu Val Trp Lys Ser Ala Glu Gly Thr Phe Phe Ile Asn Lys Thr Glu
145                 150                 155                 160

Ile Glu Asp Phe Pro Arg Phe Pro His Arg Gly Leu Leu Leu Asp Thr
                165                 170                 175

Ser Arg His Tyr Leu Pro Leu Ser Ser Ile Leu Asp Thr Leu Asp Val
            180                 185                 190

Met Ala Tyr Asn Lys Leu Asn Val Phe His Trp His Leu Val Asp Asp
            195                 200                 205

Pro Ser Phe Pro Tyr Glu Ser Phe Thr Phe Pro Glu Leu Met Arg Lys
210                 215                 220

Gly Ser Tyr Asn Pro Val Thr His Ile Tyr Thr Ala Gln Asp Val Lys
225                 230                 235                 240

Glu Val Ile Glu Tyr Ala Arg Leu Arg Gly Ile Arg Val Leu Ala Glu
                245                 250                 255

Phe Asp Thr Pro Gly His Thr Leu Ser Trp Gly Pro Gly Ile Pro Gly
                260                 265                 270

Leu Leu Thr Pro Cys Tyr Ser Gly Ser Glu Pro Ser Gly Thr Phe Gly
                275                 280                 285

Pro Val Asn Pro Ser Leu Asn Asn Thr Tyr Glu Phe Met Ser Thr Phe
            290                 295                 300

Phe Leu Glu Val Ser Ser Val Phe Pro Asp Phe Tyr Leu His Leu Gly
305                 310                 315                 320

Gly Asp Glu Val Asp Phe Thr Cys Trp Lys Ser Asn Pro Glu Ile Gln
                325                 330                 335

Asp Phe Met Arg Lys Lys Gly Phe Gly Glu Asp Phe Lys Gln Leu Glu
                340                 345                 350

Ser Phe Tyr Ile Gln Thr Leu Leu Asp Ile Val Ser Ser Tyr Gly Lys
            355                 360                 365

Gly Tyr Val Val Trp Gln Glu Val Phe Asp Asn Lys Val Lys Ile Gln
            370                 375                 380

Pro Asp Thr Ile Ile Gln Val Trp Arg Glu Asp Ile Pro Val Asn Tyr
385                 390                 395                 400

Met Lys Glu Leu Glu Leu Val Thr Lys Ala Gly Phe Arg Ala Leu Leu
                405                 410                 415

Ser Ala Pro Trp Tyr Leu Asn Arg Ile Ser Tyr Gly Pro Asp Trp Lys
                420                 425                 430

Asp Phe Tyr Ile Val Glu Pro Leu Ala Phe Glu Gly Thr Pro Glu Gln
            435                 440                 445

Lys Ala Leu Val Ile Gly Gly Glu Ala Cys Met Trp Gly Glu Tyr Val
            450                 455                 460

Asp Asn Thr Asn Leu Val Pro Arg Leu Trp Pro Arg Ala Gly Ala Val
465                 470                 475                 480
```

```
Ala Glu Arg Leu Trp Ser Asn Lys Leu Thr Ser Asp Leu Thr Phe Ala
            485                 490                 495

Tyr Glu Arg Leu Ser His Phe Arg Cys Glu Leu Leu Arg Gly Val
        500                 505                 510

Gln Ala Gln Pro Leu Asn Val Gly Phe Cys Glu Gln Glu Phe Glu Gln
        515                 520                 525

Thr

<210> SEQ ID NO 10
<211> LENGTH: 195
<212> TYPE: DNA
<213> ORGANISM: Artificial Sequence
<220> FEATURE:
<223> OTHER INFORMATION: Modified JeT Promoter
<220> FEATURE:
<221> NAME/KEY: promoter
<222> LOCATION: (1)..(195)
<223> OTHER INFORMATION: Modified JeT Promoter

<400> SEQUENCE: 10
gaattcgggc ggagttaggg cggagccaat cagcatgcac cattccaaaa gttgcctttt      60
atggctgggc ggagaatggg cggtgaacac caatgattat ataaggacac accaggtgtg    120
gcacagctag ttccatcaca gccagccagc ccaacagacg tcttgtttgt ggatccctgt    180
gatcatcact tgaca                                                     195

<210> SEQ ID NO 11
<211> LENGTH: 140
<212> TYPE: DNA
<213> ORGANISM: Artificial Sequence
<220> FEATURE:
<223> OTHER INFORMATION: Synthetic Intron
<220> FEATURE:
<221> NAME/KEY: Intron
<222> LOCATION: (1)..(140)

<400> SEQUENCE: 11
gtaagtcact gactgtctat acctgggaaa gggtgggcag gagatagggc agtgcaggaa      60
aagtggcact ataaaccctg cagccctagg aatacatcta gacaattgta ctaaccttct    120
tctctttcct ctcctgacag                                                140

<210> SEQ ID NO 12
<211> LENGTH: 12
<212> TYPE: DNA
<213> ORGANISM: Artificial Sequence
<220> FEATURE:
<223> OTHER INFORMATION: Motif Ten Element Consensus Sequence
<220> FEATURE:
<221> NAME/KEY: misc_feature
<222> LOCATION: (1)..(12)
<223> OTHER INFORMATION: Motif Ten Element (MTE) Consensus Sequence

<400> SEQUENCE: 12
csarcssaac gs                                                         12

<210> SEQ ID NO 13
<211> LENGTH: 78
<212> TYPE: DNA
<213> ORGANISM: Artificial Sequence
<220> FEATURE:
<223> OTHER INFORMATION: Portion of JeT Promoter
<220> FEATURE:
<221> NAME/KEY: promoter
<222> LOCATION: (1)..(78)
<223> OTHER INFORMATION: Portion of JeT Promoter
```

<400> SEQUENCE: 13
atgattatat aaggacgcgc cgggtgtggc acagctagtt ccgtcgcagc cgggatttgg    60
gtcgcggttc ttgtttgt                                                  78

<210> SEQ ID NO 14
<211> LENGTH: 78
<212> TYPE: DNA
<213> ORGANISM: Artificial Sequence
<220> FEATURE:
<223> OTHER INFORMATION: Modified Portion of JeT Promoter
<220> FEATURE:
<221> NAME/KEY: promoter
<222> LOCATION: (1)..(78)
<223> OTHER INFORMATION: Modified portion of JeT promoter with addition
      of MTE (without CpG) and DPE consensus sequence

<400> SEQUENCE: 14
atgattatat aaggacgcgc cgggtgtggc acagctagtt ccgtcgcagc cggccagccc    60
aacagacgtc ttgtttgt                                                  78

<210> SEQ ID NO 15
<211> LENGTH: 78
<212> TYPE: DNA
<213> ORGANISM: Artificial Sequence
<220> FEATURE:
<223> OTHER INFORMATION: Modified Portion of JeT Promoter
<220> FEATURE:
<221> NAME/KEY: promoter
<222> LOCATION: (1)..(78)
<223> OTHER INFORMATION: Modified portion of JeT promoter with addition
      of MTE and DPE consensus sequence

<400> SEQUENCE: 15
atgattatat aaggacgcgc cgggtgtggc acagctagtt ccgtcgcagc cctcgagccg    60
agcagacgtc ttgtttgt                                                  78

<210> SEQ ID NO 16
<211> LENGTH: 78
<212> TYPE: DNA
<213> ORGANISM: Artificial Sequence
<220> FEATURE:
<223> OTHER INFORMATION: Modified Portion of JeT Promoter
<220> FEATURE:
<221> NAME/KEY: promoter
<222> LOCATION: (1)..(78)
<223> OTHER INFORMATION: Modified portion of JeT promoter with addition
      of MTE and DPE consensus sequence.

<400> SEQUENCE: 16
atgattatat aaggacgcgc cgggtgtggc acagctagtt ccgtcgcagc cctcgaaccg    60
aacagacgtc ttgtttgt                                                  78

<210> SEQ ID NO 17
<211> LENGTH: 10
<212> TYPE: DNA
<213> ORGANISM: Artificial Sequence
<220> FEATURE:
<223> OTHER INFORMATION: Alternative MTE Form
<220> FEATURE:
<221> NAME/KEY: misc_feature
<222> LOCATION: (1)..(10)
<223> OTHER INFORMATION: Portion of Alternative MTE Form

<400> SEQUENCE: 17
cgagccgagc                                                           10

```
<210> SEQ ID NO 18
<211> LENGTH: 10
<212> TYPE: DNA
<213> ORGANISM: Artificial Sequence
<220> FEATURE:
<223> OTHER INFORMATION: Alternative MTE Form
<220> FEATURE:
<221> NAME/KEY: misc_feature
<222> LOCATION: (1)..(10)
<223> OTHER INFORMATION: Portion of Alternative MTE Form

<400> SEQUENCE: 18
cgaaccgaac                                                              10
```